US011097275B2

(12) United States Patent
Viovy et al.

(10) Patent No.: US 11,097,275 B2
(45) Date of Patent: *Aug. 24, 2021

(54) DEVICE FOR MANIPULATION OF PACKETS IN MICRO-CONTAINERS, IN PARTICULAR IN MICROCHANNELS

(71) Applicants: INSTITUT CURIE, Paris (FR); CENTRE NATIONAL DE LA RECHERCHE SCIENTIFIQUE, Paris (FR)

(72) Inventors: Jean-Louis Viovy, Paris (FR); Max Chabert, Paris (FR); Kevin Dorfman, Minneapolis, MN (US)

(73) Assignees: INSTITUT CURIE, Paris (FR); CENTRE NATIONALE DE RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/784,736

(22) Filed: Feb. 7, 2020

(65) Prior Publication Data

US 2020/0171499 A1 Jun. 4, 2020

Related U.S. Application Data

(60) Continuation of application No. 15/392,189, filed on Dec. 28, 2016, now Pat. No. 10,661,278, which is a
(Continued)

(30) Foreign Application Priority Data

Sep. 9, 2004 (EP) ..................................... 04292173
Dec. 14, 2004 (EP) ..................................... 04292995

(51) Int. Cl.
| | | |
|---|---|---|
| *B01L 3/00* | (2006.01) | |
| *B01F 13/00* | (2006.01) | |
| *B01J 19/00* | (2006.01) | |
| *B01L 7/00* | (2006.01) | |
| *F04B 19/00* | (2006.01) | |
| *G01N 35/08* | (2006.01) | |

(Continued)

(52) U.S. Cl.
CPC .... *B01L 3/502784* (2013.01); *B01F 13/0071* (2013.01); *B01F 13/0076* (2013.01); *B01J 19/0093* (2013.01); *B01L 3/5027* (2013.01); *B01L 3/502723* (2013.01); *B01L 7/525* (2013.01); *C12Q 1/686* (2013.01); *F04B 19/006* (2013.01); *G01N 35/08* (2013.01); *B01J 2219/0086* (2013.01); *B01J 2219/0097* (2013.01); *B01J 2219/00783* (2013.01); *B01J 2219/00788* (2013.01); *B01J 2219/00824* (2013.01); *B01J 2219/00831* (2013.01); *B01J 2219/00833* (2013.01); *B01J 2219/00837* (2013.01); *B01J 2219/00853* (2013.01); *B01J 2219/00873* (2013.01); *B01J 2219/00889* (2013.01); *B01J 2219/00891* (2013.01); *B01L 2200/0605* (2013.01); *B01L 2200/0673* (2013.01); *B01L 2200/0684* (2013.01); *B01L 2300/0816* (2013.01); *B01L 2300/0838* (2013.01); *B01L 2300/1816* (2013.01); *B01L 2300/1827* (2013.01); *B01L 2300/1894* (2013.01); *B01L 2400/0415* (2013.01); *B01L 2400/0427* (2013.01); *B01L 2400/0493* (2013.01); *G01N 2015/003* (2013.01); *G01N 2015/0053* (2013.01); *G01N 2035/1037* (2013.01)

(58) Field of Classification Search
CPC ......... B01L 3/502784; B01L 3/502723; B01L 2200/0605; B01L 2200/0673; B01L 2300/0838; B01L 2400/0415; B01L 2400/0427; B01L 3/00; B01L 3/5027; B01L 7/525; B01L 2200/0684; B01L 2300/1816; B01L 2300/1827; B01L 2300/1894; B01L 2300/0816; B01L 2400/0493; C12Q 1/686; C12Q 2563/159; C12Q 2531/113; C12Q 1/6806; B01F 13/0076; B01F 13/0071; B01J 19/0093; B01J 2219/00783; B01J 2219/00788; B01J 2219/00824; B01J 2219/00831; B01J 2219/00833; B01J 2219/00837; B01J 2219/00853; B01J 2219/0086; B01J 2219/00873; B01J 2219/0086; B01J 2219/00891; B01J 2219/0097; F04B 19/006; G01N 35/08; G01N 2015/003; G01N 2015/0053; G01N 2035/1037; C12M 21/00; C12N 15/1096
See application file for complete search history.

(56) References Cited

U.S. PATENT DOCUMENTS

| | | | |
|---|---|---|---|
| 6,130,098 | A | 10/2000 | Handique et al. |
| 6,146,103 | A | 11/2000 | Lee et al. |

(Continued)

FOREIGN PATENT DOCUMENTS

| | | | |
|---|---|---|---|
| EP | 1 348 546 A2 | 10/2003 | |
| FR | 2 794 039 A1 | 12/2000 | |

(Continued)

OTHER PUBLICATIONS

Duffy el al , Rapid Prototyping of Microfluicic Systems in Poly(dimethylsiloxane), 1998, Anal. Chem., 70, 4974-4984.

(Continued)

*Primary Examiner* — Narayan K Bhat
(74) *Attorney, Agent, or Firm* — Oliff PLC

(57) ABSTRACT

A microfluidic device for performing physical, chemical or biological treatment to at least one packet without contamination.

13 Claims, 8 Drawing Sheets

Specification includes a Sequence Listing.

Related U.S. Application Data division of application No. 11/662,362, filed as application No. PCT/IB2005/052951 on Sep. 9, 2005, now Pat. No. 9,566,558.

(51) Int. Cl.
  *C12Q 1/686* (2018.01)
  *G01N 15/00* (2006.01)
  *G01N 35/10* (2006.01)

(56) References Cited

U.S. PATENT DOCUMENTS

| | | |
|---|---|---|
| 6,294,063 B1 | 9/2001 | Becker et al. |
| 6,565,727 B1 | 5/2003 | Shenderov |
| 6,641,708 B1 | 11/2003 | Becker et al. |
| 6,790,011 B1 | 9/2004 | Le Pesant et al. |
| 6,911,132 B2 | 6/2005 | Pamula et al. |
| 7,556,776 B2 | 7/2009 | Fraden et al. |
| 7,718,578 B2 | 5/2010 | Griffiths et al. |
| 7,927,797 B2 | 4/2011 | Nobile et al. |
| 7,968,287 B2 | 6/2011 | Griffiths et al. |
| 8,293,471 B2 | 10/2012 | Gregg et al. |
| 2002/0058332 A1 | 5/2002 | Quake et al. |
| 2003/0127329 A1 | 7/2003 | DeVoe et al. |
| 2004/0258571 A1 | 12/2004 | Lee et al. |
| 2005/0221339 A1 | 10/2005 | Griffiths et al. |
| 2005/0272159 A1 | 12/2005 | Ismagilov et al. |
| 2006/0078888 A1 | 4/2006 | Griffiths et al. |
| 2006/0078893 A1 | 4/2006 | Griffiths et al. |
| 2006/0153924 A1 | 7/2006 | Griffiths et al. |
| 2006/0154298 A1 | 7/2006 | Griffiths et al. |
| 2006/0163385 A1 | 7/2006 | Link et al. |
| 2007/0003442 A1 | 1/2007 | Link et al. |
| 2007/0052781 A1 | 3/2007 | Raden et al. |
| 2007/0092914 A1 | 4/2007 | Griffiths et al. |
| 2007/0184489 A1 | 8/2007 | Griffiths et al. |
| 2007/0195127 A1 | 8/2007 | Ahn et al. |
| 2009/0005254 A1 | 1/2009 | Griffiths et al. |
| 2009/0131543 A1 | 5/2009 | Weitz et al. |
| 2009/0197248 A1 | 8/2009 | Griffiths et al. |
| 2009/0197772 A1 | 8/2009 | Griffiths et al. |
| 2010/0105866 A1 | 4/2010 | Raden et al. |
| 2010/0210479 A1 | 8/2010 | Griffiths et al. |

FOREIGN PATENT DOCUMENTS

| | | |
|---|---|---|
| WO | 00/73655 A1 | 12/2000 |
| WO | 2003/020981 A1 | 3/2003 |

OTHER PUBLICATIONS

Datasheet Wire, Retrieved from the internet URL:http//dictionary.reference.com/browse/wire, printed on Aug. 5, 2010, p. 1.
Zhou et al, High temperature transport properties of polyphosphazene membranes for direct methanol fuel cells, 2003, Elecrochimica Acta, 48, 2173-2180.
Jones et al, Frequency-Based Relationship of Electrowetting and Dielectrophoretic Liquid Microactuation, 2003, Langmuir, 19, 7646-7651.
Oct. 23, 2014 Office Action issued in European Application No. 05 782 951.7.
Zhang et al, "Theoretical Prediction of Electric Field-Enhanced Coalescences of Speherical Drops," AIChE Journal, vol. 41, No. 7, pp. 1629-1639, Jul. 1995.
Washizu, "Electrostatic Actuation of Liquid Droplets for Microreactor Application," IEEE Transactions on Industry Applications, vol. 34, No. 4, pp. 732-737, Jul./Aug. 1998.
Schwartz et al., "Droplet-based chemistry on a programmable micro-chip," Lab Chip, vol. 4, pp. 11-17 (2004).
Velev et al., "On-chip manipulation of free droplets," Nature, vol. 426, pp. 515-516, Dec. 2003.
Curcio et al., "Continuous Segmented-Flow Polymerase Chain Reaction for High-Throughput Miniaturized DNA Amplification," Analytical Chemistry, vol. 75, No. 1, pp. 1-7, Jan. 1, 2003.
Park et al., "Cylindrical Compact Thermal-Cycling Device for Continuous-Flow Polymerase Chain Reaction," Analytical Chemistry, vol. 75, No. 21, pp. 6029-6033, Nov. 1, 2003.
Schnelle et al., "Dielectrophoretic manipulation of suspended sibmicron particles," Electrophoresis, vol. 21, pp. 66-73 (2000).
Durr et al., "Microdevices for manipulation and accumilation of micro- and nanoparticles by dielectrophoresis," Electrophoresis, vol. 24, pp. 722-731 (2003).
Olbricht et al., "The Interaction and Coalescence of Liquid Drops in Flow through a Capillary Tube," Journal of Colloid and Interface Science, vol. 120, No. 1 pp. 229-244, Nov. 1987.
Atten, "Electrocoalescence of water droplets in an insulating liquid," Journal of Electrostatics, vol. 30, pp. 259-270 (1993).
Paik et al., "Electrowetting-based droplets mixers for microfluidic systems," Lab Chip, vol. 3, pp. 28-33, Feb. 3, 2003.
Tice et al., "Formation of Droplets and Mixing in Myultiphase Microfluidics at Low Values of the Reynolds and the Capillary Numbers," Langmuir, vol. 19, pp. 9127-9133, Aug. 12, 2003.
Jan. 21, 2014 Office Action issued in Japanese Patent Application No. 2012-237242.
Zhang et al, Commonly Used Surfactant, Tween 80, Improves Absorption of P-Glycoprotein Substrate, Digoxin, in Rats, 2003, Arch Pharm Res, 26, 768-772. (Year:2003).
Data sheet Pluronic F108, p. 1, 2004 (Year: 2004).

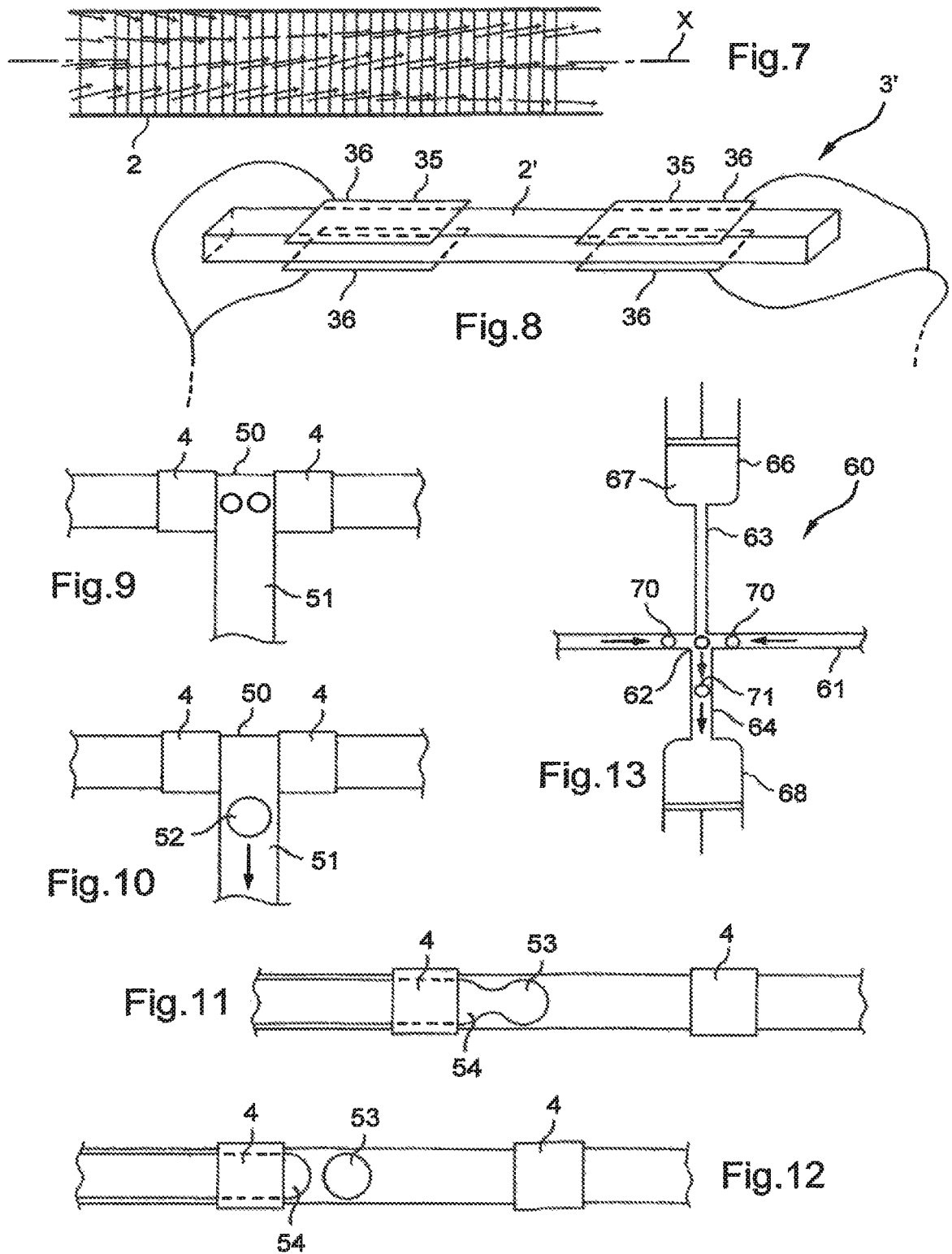

SEQUENCE LISTING

```
<160> NUMBER OF SEQ ID NOS: 5

<210> SEQ ID NO 1
<211> LENGTH: 30
<212> TYPE: DNA
<213> ORGANISM: Artificial
<220> FEATURE:
<223> OTHER INFORMATION: Primer

<400> SEQUENCE: 1
cgcattgcgg tatctagaac cggtgacgtc                                      30

<210> SEQ ID NO 2
<211> LENGTH: 18
<212> TYPE: DNA
<213> ORGANISM: Artificial
```

```
<220> FEATURE:
<223> OTHER INFORMATION: Primer

<400> SEQUENCE: 2
agcttggagc gaacgacc                                                         18

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
atctgctgca tctgcttgga gccca                                                 25

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ggcgacctgg aagtccaact                                                       20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ccatcagcac cacagccttc                                                       20
```

DEVICE FOR MANIPULATION OF PACKETS IN MICRO-CONTAINERS, IN PARTICULAR IN MICROCHANNELS

This application is a Continuation of application Ser. No. 15/392,189, filed Dec. 28, 2016, which is a Divisional of application Ser. No. 11/662,362, filed Jun. 20, 2007 (now U.S. Pat. No. 9,566,558), which is a national stage of PCT/IB2005/052951, filed Sep. 9, 2005, which claims priority to EP 04292173.4, filed Sep. 9, 2004, and EP 04292995.0, filed Dec. 14, 2004. The entire contents of the prior applications are hereby incorporated by reference herein in their entireties.

The present invention relates to a device for manipulation of packets in micro-containers, in particular in microchannels.

As used herein, «packet» refers to compartmentalized matter and may refer to a fluid packet, an encapsulated packet and/or a solid packet.

A fluid packet refers to one or more packets of liquids or gases. A fluid packet may refer to a droplet or bubble of a liquid or gas. A fluid packet may refer to a droplet of water, a droplet of reagent or sample, a droplet of solvent, a droplet of solution, a particle suspension or cell suspension, a droplet of an intermediate product, a droplet of a final reaction product or a droplet of any material. An example of a fluid packet is a droplet of aqueous solution suspended in oil. In a preferred embodiment, a fluid packet refers to a droplet of water or a droplet of solution.

An encapsulated packet refers to a packet enclosed by a layer of material. The surface of an encapsulated packet may be coated with a reagent, a sample, a particle or cell, an intermediate product, a final reaction product, or any material. An example of an encapsulated packet is a lipid vesicle containing an aqueous solution of reagent suspended in water.

A packet may contain for instance a vesicle or other microcapsule of liquid or gas that may contain a reagent, a sample, a particle, a dead cell or alive cell, an intermediate product, a final reaction product, or any material.

A solid packet refers to a solid material, for example biological material, that may contain, or be covered with, a reagent, a sample, a particle or cell, an intermediate product, a final reaction product, or any material. An example of a solid packet is a latex microsphere with reagent bound to its surface suspended in an aqueous solution. A packet may contain a crystal, a polycrystalline material or a vitreous material.

Packets may be made to vary greatly in size and shape, and may have a maximum dimension between about 100 nm and about 1 cm.

Droplet systems may consist in water-based droplets in oil or a fluorinated solvent, or "oily" (water immiscible) droplets in an aqueous solvent. The fluid involved in the droplet system of the invention may be any kind of fluid, aqueous, organic, mineral, hydrophilic, or hydrophobic, including water based buffers, biological fluids, hydroorganic solvents, liquids made of molecules with carbon-carbon backbone, Si—Si backbone (silicone), heteroatom backbone (such as for example polyethylene glycol), or ionic liquids. Droplet systems have received much attention in microfluidics as a method for producing precise emulsions, as discrete microreactors for polymerase chain reaction (PCR), for the measurement of fast kinetics, and for the dispersion-free transport and manipulation of sample aliquots. Considerable efforts have thus been developed in the last years to create and/or manipulate microdroplets. Some devices use hydrophobic forces, by moving such droplets in microchannel combining some hydrophilic and some hydrophobic portions. For instance, U.S. Pat. No. 6,130,098 discloses a method for moving microdroplets, comprising:

providing a microdroplet transport channel having one or more hydrophobic regions and in communication with a gas source, introducing liquid into said channel under conditions such as the liquid stops at one of the hydrophobic regions, separating a microdroplet by increasing the pressure applied by the gas source so as to let such droplet moves over the hydrophobic region.

This approach imposes that different droplets be in contact with the same solid surface, and is thus prone to contamination.

Manipulation of droplets on planar arrays of electrodes by electrowetting has also become very popular, since it allows one to address droplets to diverse locations and along complex and programmable paths. For instance, U.S. Pat. No. 6,294,063 discloses an apparatus for programmably manipulating a plurality of packets, such packets optionally being droplets, said apparatus comprising a reaction surface configured to provide an interaction site for such packets, an inlet port, means to generate manipulation forces upon said packets, the forces being capable of programmably moving said packets about said reaction surface along arbitrarily chosen paths, and a position sensor.

U.S. Pat. No. 6,565,727 also discloses a device for manipulating a droplet of a polar liquid, comprising an upper and lower surface, defining between them a gap, said upper surface comprising a plurality of interdigitated electrodes, and said lower surface comprising a common counterelectrode. The device further comprises insulating layers between said electrodes and said gap, and a non-polar liquid positioned in the gap. In this device, a droplet can be maintained on top of a first electrode on the upper surface, by applying a potential between said electrode and the counterelectrode on the lower surface, making the upper surface wetting for the droplet in the vicinity of said first electrode. Then, the droplet can be moved to a second electrode on the upper surface interdigitated with said first electrode, by suppressing the potential difference between the first electrode and the counterelectrode, and applying a potential difference between the second electrode and the counterelectrode to make said second electrode wetting to the fluid.

Electrowetting can also be used to mix two different droplets, as described e.g. in M. Washizu, *IEEE Trans. Ind. Appl.*, 34, 732-737 (1998). Mixing of droplets containing e.g. two reagents or a sample and a reagent is a key technological step for developing microfluidic integrated systems or "lab-on-chips".

The format of a planar array of electrodes required by electrowetting, however, has severe drawbacks. The fabrication of the array of electrodes is complex, and becomes extremely expensive and technically demanding for surfaces exceeding a few square cm. Therefore, transporting droplets on large distances, e.g. more than 10 cm, is impractical. Also, for liquid droplets the surface should be kept horizontal and relatively vibration free, to avoid unwanted motion of droplets under the action of gravity or acoustic waves. Droplet manipulation in planar format may also be limited by droplet evaporation, the latter being a serious hindrance in quantitative biochemistry applications, since reaction yields are highly sensitive to concentration. Electrowetting may further introduce surface contamination. Another limitation is that electrowetting can only work with liquids, so that it cannot be used to transport solid objects.

Dielectrophoresis is another way of transporting and mixing droplets or solid objects such as cells or latex particles. For instance, Schwartz et al. in Lab Chip, 4, 11-17 (2004) discloses a programmable fluid processor, in which droplets can be moved and mixed on top of an array of electrodes, by energizing sequentially electrodes in the array. This method, however, also requires a complex array of electrodes on a planar surface, and thus shares many of the drawbacks of electrowetting. In another instance, Velev et al., Nature, 426, 515-516 (2003) describes a process for moving and mixing droplets which are floating on a layer of fluorinated oil, where the oil is in contact with a pattern of electrodes. This eliminates the contamination problems inherent in electrowetting, but still requires fabricating a complex array of electrodes.

Transporting and mixing droplets in an elongated microchannel, or in a network of connected microchannels is more robust to the above problems. For instance, it avoids evaporation, and allows transport on long distances by simple hydrodynamic mobilization of a carrier fluid surrounding the droplets. Droplets can thus be transported in capillaries several meters long, and used as microreactors, as disclosed e.g. in Curcio and Roeraade, Anal. Chem., 75, 1-7 (2003). When interaction with the walls is well controlled, all droplets move at the same velocity, and very stable trains are achieved. However, the systems of this kind suffer from contamination between droplets, which has been attributed to the formation of small satellite drops in the flow. Park et al. *Anal. Chem.* 2003, 75, 6029-6033, has proposed a system in which numerous aqueous sample plugs are separated by plugs of air. However, wall treatments are not sufficient to completely eliminate contamination, so it is sometimes necessary to include a "wash" droplet between samples. In addition, bubbles in the stream may introduce irregularities in the thermal history of the droplets, making this technique less attractive for quantitative applications It was also proposed to manipulate solid particles or cells in microchannels by dielectrophoresis. Dielectrophoresis uses a force exerted on a particle with a dielectric constant different from that of the surrounding medium in a gradient of electric field. Different types of arrangements were used to date for the application of dielectophoresis in microchannels. In a first one, an array of closely spaced interdigitated electrodes locally creates lines of high field gradient in which particles are attracted. Optionally, these lines can be shifted in time by alternately energizing different series of electrodes, said method being called □travelling wave dielectrophoresis□. For instance, Schnelle et al., *Electrophoresis*, 21, 66-73 (2000) discloses a method for sorting particles, in which they are deflected by travelling wave dielectrophoresis between a multiplicity of electrodes in an interdigitated arrangement, and energized sequentially with a four phase alternating electric signal. By using pairs of electrodes of different shapes facing each other across the microchannel, and applying a potential difference between them, it is also possible to create different kinds of dielectrophoretic traps, cages or deflecting electrodes, as described e.g. in Durr et al., *Electrophoresis*, 24, 722-731 (2003).

These dielectrophoretic devices present some advantages upon planar systems. In particular, they are more robust to tilting or vibration. However, they still require complex microfabrication, and are expensive to fabricate.

Another key hurdle in the development of microchannel droplet systems, especially for microreactor applications, is the mixing of samples or reagents from different sources.

For this, one needs to coalesce two droplets, but Laplace and hydrodynamic forces tend to make this coalescence difficult. When arriving simultaneously at a T-intersection, one drop simply follows the second one into the T without coalescing. Coalescence can be forced by contact charging the droplets, but this could be a major source of contamination in PCR and other biological systems. Once introduced into a channel, a smaller droplet trailing a larger one may eventually coalesce with it, since the smaller droplet moves with a higher average velocity. However, this is not a rationale strategy in microfluidics, since film drainage between the droplets is very slow, leading to coalescence distances between 30-100 tube diameters (Olbricht and Kung, *J. Colloid Interface Sci.*, 120, 229-244 (1987)). Moreover, under certain conditions (relative droplet sizes, viscosities, etc.) no coalescence is achieved, and the coalescence time or position are not very reproducible.

Consequently, there exists a strong need for a device and method providing reproducible, contamination-free droplet manipulation, in particular coalescence, in microchannels or closed microfluidic systems.

An object of the present invention among others is to provide such device and method.

The present invention relates to, according to one of its aspects, a microfluidic device for deforming, in particular splitting, at least one packet, or displacing at least two packets towards each other, in particular for collapsing, said device comprising:

a microchannel having an axis, packet manipulation means comprising at least one of:
   a generator unit, and an electrode assembly coupled to the generator unit and configured for creating inside at least one portion of the microchannel an electric field which is substantially collinear to the axis (X) of the microchannel, wherein the generator unit is capable of generating the electric field with such an amplitude and frequency that the electric field causes the at least one packet to deform, or the at least two packets to displace towards each other in the microchannel,
   at least one side channel with a first end in connection with a portion of said microchannel and a second end in connection with a delivery system suitable for delivering a solution, with in particular a surfactant, able to alter the interfacial tension between said at least two packets or said at least one packet and the environment thereof, said delivery system being configured to deliver said solution into said microchannel at least during the passage of said packet(s) in said portion of the microchannel.

In other words, the manipulation of the packet(s) with the device according to the present invention may be carried out by generating an appropriate electric field, or by modifying the surface tension of a liquid packet, or by combining both techniques.

The interfacial tension may be modified, preferably decreased, by a factor of at least 20%, and more preferably 50%.

When two packets are introduced in the portion of the microchannel in which the electric field is applied to cause two packets to collapse, dipoles are created by the electric field in the packets, said dipoles being oriented substantially along the axis of the microchannel such that the packets attract each other and collapse.

The expression "substantially collinear" means that the average of the direction of the electric field makes with the axis of the microchannel an angle smaller than 45°, for example smaller than 30°, preferably smaller than 20°, and more preferably smaller than 10° or 5°.

The invention may be used for inducing the collapse of two packets, and for example the coalescence of two droplets inside the microchannel.

The general physical phenomenon called "electrocoalescence" is disclosed in P. Atten, J. Electrostat. 30, 259 (1993). As electrophoretic forces, and in contrast with dielectrophoresis, electrocoalescence does not require a field gradient.

When the packet is a cell, or contains several cells, the invention may be used to induce electroporation of such cell or multiplicity of cells.

The invention may also be used to split a packet into several packets of smaller size, and for example to extract from a droplet one or several droplets of smaller size.

A micro-container according to the invention may have any size. Preferably, it has at least one dimension smaller than one millimeter. In an embodiment, said micro-container is a micro-capillary with a diameter smaller than 1 mm. For instance, at least one dimension in cross-section of said capillary is preferably comprised between 100 µm and 1 mm. In an embodiment, at least one dimension of said capillary is comprised between about 10 nm and 100 µm, preferable between 1 µm and 100 µm. In another embodiment, said micro-container is a micro-fabricated microchannel with a thickness smaller than 1 mm. In some embodiments, the thickness of said microchannel is preferably comprised between about 100 µm and 1 mm. The thickness of said microchannel may be comprised between about 10 nm and 100 µm, preferably between 1 µm and 100 µm.

In the present invention, "micro-container", in particular "microchannel", means a volume at least partly enclosed by solid surfaces, said volume being small. Preferably, a micro-container, in particular a microchannel, in the invention has a surface/volume ratio substantially greater than 1 $mm^{-1}$, preferably greater than 4 $mm^{-1}$, for example greater than 10 $mm^{-1}$, possibly greater than 1 $µm^{-1}$. Microchannels also encompass nanochannels.

In an embodiment, the microchannel is preferably elongated, i.e. the dimension along its axis is larger by a factor of 3, preferably by a factor of 10, for example by a factor of 100 or 1000, than along any other direction perpendicular to said axis.

The axis of the microchannel may be rectilinear or not.

The microchannel may have a cross-section which is constant or not. The section may be for example circular, ellipsoidal, rectangular, square or with a bowl shape.

In the present invention, "thickness" means the smallest inner distance in cross section between two opposite sides of the microchannel. As a matter of example, for a cylindrical microchannel having a circular cross section, the thickness is the diameter. For a slit-like microchannel having a rectangular cross section, the thickness is the length of the small side of the rectangle.

The thickness of the microchannel can take any value between a few nm and a few mm. Preferably, the thickness is comprised between 1 µm and 1 mm. Still preferably, the length of the microchannel along its axis, may be chosen to be at least 10 times larger than the thickness. The microchannel may have a length chosen between 10 mm and several meters, for example between 1 cm and 50 cm.

Preferably, the portion of the microchannel in which the electric field is substantially collinear to the axis of the microchannel has a length along said axis at least as large as the thickness of the microchannel, and smaller than the total length of the microchannel. In a preferred embodiment of the invention, the length of said portion of the microchannel is comprised between about 1 and about 100 times the thickness of said portion, and preferably between about 1 and about 10 times the thickness of said portion.

The microchannel may be rigid or flexible and comprises for example a tube made of a flexible non-electrically-conducting material.

The micro-container, in particular the microchannel, may be made of at least one material selected among: fused silica glass, PDMS (polydimethylsiloxane), PMMA (polymethylmethacrylate), any kind of elastomer or plastics, such as for example polyethylene, polyimide, epoxy, Teflon®, Parylene®, polystyrene, polyethylene terephtalate, fluoropolymer, polyester, cyclic olefin copolymer, non-conducting oxide such as, for example, glass, silicon dioxide, diamond, non-conductive ceramics, a silicone, an elastomer, a glassy material, a mineral material, a ceramic, a polymer, a thermoplastic polymer, a thermocurable resin, a photocurable resin, a copolymer In an exemplary embodiment of the invention, the microchannel has at least one inlet port, and/or at least one outlet port. Optionally, at least one of said ports can be connected to one or several reservoirs, to one or several pumps, to one or several detectors or sensors or to one or several sampling devices.

The microchannel may be part of a network of connected microchannels.

In a preferred embodiment of the invention, said electrode assembly is electrically insulated from an inside surface of the microchannel, for example by an insulating material. The insulating material may have a thickness of at least 1 nm, for example at least 10 nm, preferably at least 100 nm, most preferably of at least 1 µm, for example up to several tens or hundreds µm. Typically, thicker insulating layers may be preferred for larger microchannels. This insulating material may be made out of for example polymeric material, e.g. for example polyethylene, polyimide, epoxy, Teflon®, Parylene®, PMMA, polystyrene, polyethylene terephtalate, fluoropolymer, polyester, cyclic olefin copolymer, PDMS, non-conducting oxide such as, for example, glass, silicon dioxide, diamond, non-conductive ceramics.

Preferably, the electrode assembly comprises at least two electrodes axially spaced along the axis of the microchannel by a distance long enough for the electric field between the electrodes to be substantially collinear to the axis of the microchannel. Each electrode may be symmetric relative to the axis of the microchannel. Advantageously, at least one of said electrodes comprises at least two equipotential portions facing each other across the microchannel. At least one of said electrodes may be monolithic having for example a cylindrical surface surrounding the microchannel. In a variant, at least one of said electrodes is composite, i.e. made out of a plurality of pieces, comprising for example at least two substantially parallel equipotential plates sandwiching the microchannel. The electrodes may also have a shape other than those described above.

This is different from the prior art as disclosed in patent application FR 2 794 039 or in Paik et al., Lab Chip, 3, 28-33 (2003) wherein manipulation of the droplets is obtained by an opposite configuration, i.e. applying a potential difference between two planar electrodes facing each other across the chamber in which the droplet to be manipulated is contained.

Preferably, the electrodes are spaced by a gap having a length that is greater than the thickness of the microchannel, preferably greater than twice the thickness.

The generator unit comprises advantageously at least one of a current and a voltage generator, configured to create a difference of potential between said two electrodes, preferably an alternating potential.

Advantageously, the electrode assembly is configured so that in at least one cross section of the microchannel the amplitude of the electric field varies less than a factor 10, preferably less than a factor 5, better less than a factor 2, and preferably is substantially uniform, in particular in the gap between the electrodes.

The electric field generated by the generator unit via the electrode assembly may have any temporal profile, for example continuous, variable or alternating (AC), or a combination of such temporal profiles. For instance, the electric field may be an AC field with variable frequency or root mean squared (RMS) amplitude, or a superposition of continuous and AC components.

By "AC field", we mean any field periodic in time and with a zero time average. Non limiting examples of AC fields according to the invention are sinusoidal, square or sawtooth AC fields.

The generator unit is preferably capable of generating an AC electric field with a frequency ranging from about 0.01 Hz to about 1 GHz, preferably from about 1 Hz to about 10 MHz.

The coalescence of droplets is efficiently achieved, for instance, with frequencies between 100 Hz and 10 kHz. The aliquoting of at least one droplet is preferably achieved at frequencies lower than 50 Hz.

The generator unit may be configured for delivering a RMS voltage ranging between 1V and 30 kV, preferably between 60 V and 2 kV, depending on the nature of the packet, of the fluid surrounding the packet, of the microchannel, and on the size of the device. The voltage may increase as the size of the device increases. The RMS electric field inside the microchannel in the gap between the electrodes may range for instance between 100 V/cm and 100 kV/cm, and preferably between 500 V/cm and 20 kV/cm.

The generator unit may be configured to deliver a voltage with at least one of the amplitude and the frequency being time-related variable. For example, the amplitude and/or the frequency of the electric field may be modified as two packets come into close contact.

Advantageously, the electrode assembly is housed in a support, the latter having two separated support members assembled together via a fixing element, each support member carrying one electrode of the electrode assembly. The support may comprise at least one orifice for receiving the microchannel.

When the microchannel is connected to a side channel, said side channel may have a cross-section with dimensions comparable to those of the microchannel. Preferably, the cross-section of the side channel is smaller than this of the microchannel. In a variant, the cross-section of the side channel is larger than this of the microchannel.

The delivery system associated with said side channel may comprise pressure control means or flow control means.

Preferably, said side channel and said delivery system are configured for delivering in the microchannel a solution containing a surfactant.

The term "surfactant" means any species, molecules or combination of molecules capable of modifying the interfacial tension between two fluids. A surfactant may be for instance a tensioactive or an amphiphilic species.

The surfactant may be chosen to favor the formation of oil-in-water emulsions.

If the packets are aqueous droplets suspended in a non-aqueous liquid, said surfactants are typically surfactants with a high HLB (Hydrophilic/Lipophilic Balance), for example with HLB values larger than 15. Non-limiting examples of such surfactants are Sodium Dodecyl Sulfate (SDS), oleic acid, and CTAB.

If the packets are oily droplets in an aqueous surrounding fluid, the solution preferably contains at least one surfactant with a low HLB, for example a HLB lower than 15, and preferably lower than 10.

Numerous surfactants able to reduce the interfacial tension between an oily phase and a water phase, or to favor droplet coalescence, are recited e.g. in *Emulsions, a fundamental and practical approach*, J. S. Sjöblom Ed, Kluwer, Dordrecht (1992), or in P. Becher, *Emulsions, Theory and Practice*, $2^{nd}$ Ed, R.E. Krieger Pub. Co, Malabar, Fla. (1985).

In an exemplary embodiment of the invention, for coalescing or splitting two droplets, the device comprising a first side channel connected to the delivery system, the microchannel may be connected to a second side channel, preferably connected in regard or in close vicinity of the first side channel and configured for collecting packets formed by the coalescence or splitting of original packets.

The microchannel may be made out of a wide variety of homogeneous or composite materials. In contrast with prior art disclosed in U.S. Pat. No. 6,294,063, in which packets are manipulated onto a reaction surface configured to provide interaction sites for said packets, the wall of the microchannel according to the present invention may be made of a material, or treated with a material, reducing the risk of interaction of the packets with the wall of the microchannel in the presence of the embedding fluid. There may be no chemical interaction at all between the packets and the microchannel.

In an exemplary embodiment, the packet being a water-based droplet, the interfacial tension between the droplet and the microchannel wall is made larger than the interfacial tension between the droplet and the surrounding fluid, by treating the microchannel wall and/or by including in the droplet and/or in the fluid additives.

Numerous ways may be used to increase the surface tension between a water-based liquid and a surface. As an example, one may choose a naturally hydrophobic surface, such as fluorocarbon or polyethylene. One may also treat the surface with hydrophobic materials such as Teflon® AF, silane or fluorosilane.

The surface tension between water and hydrogenated oil-based fluids can be decreased by the presence of surface-active molecules. Numerous such surface active molecules are known in the art, and we list here only a few as a matter of examples: surfactants such as Pluronics® and Symperionics®, Triton®, Tween®, Span® 80, Tergitol®, Sodium Dodecyl Sulfate (SDS), oleic acid, methyl cellulose, hydroxyethyl and hydroxy propyl cellulose, or Coatex®. If the fluid is fluorinated, then fluorinated surfactants, such as 1H,1H,2H,2H perfluorodecan-1-ol or 1H,1H,2H,2H perfluorooctan-1-ol, are particularly suitable.

Fluorinated, water immiscible fluids may comprise at least one of the following elements: partly or fully fluorinated alkanes, alcenes or alcynes, for instance perfluoroalkanes such as perfluorodecalin. In one embodiment of the invention, the water-immiscible fluid is a mixture of fluorinated molecules, such as the fluorinated solvents of the "Freon" family, or FC fluorosurfactant, such as FC40 or FC75 (commercialized by 3M). Preferably none compound of a given molecular weight in said mixture is representing more than 75% w/w (weight by weight) of the mixture.

In an exemplary embodiment of the invention, the microchannel is filled with a fluid surrounding at least one packet, said fluid may be any liquid or gaseous fluid, provided it is not miscible in the packet or with the wall of the microchannel.

The fluid surrounding the packet may be a liquid, for example a water-immiscible organic or inorganic liquid.

The fluid may be a fluorinated liquid or gas, and the droplet may be an organic or hydroorganic liquid, optionally containing species.

In an exemplary embodiment of the invention, the packet and the surrounding fluid have different conductivities and/or different dielectric constants. For instance, the packet may have a conductivity higher than the surrounding fluid conductivity.

In an exemplary embodiment of the invention, the packet is a droplet of a first liquid suspended in an immiscible second liquid, said first liquid being more electrically conductive than the first.

The droplet may be a water based droplet. Said water based droplet may contain any kind of natural, artificial, organic or inorganic species such as, for example, biological molecules, proteins, protein complexes, enzymes, haptens, antigens, antibodies, aptamers, epitopes, nucleic acids, peptides, polysaccharides, glycopeptides, cells, cell aggregates, drugs, chemicals, latexes, living or dead organisms, viruses, organelles, liposomes, vesicles, micelles, synthetic or natural polymers, nanoparticles, luminescent molecules, quantum dots, chemical reagents, buffers, surfactants, and any combination of such species.

In another exemplary embodiment of the invention, the packet is a droplet of a water-immiscible liquid, and the surrounding fluid is a water based solution.

The invention may allow for the manipulation of packets having a size comparable with the section of the microchannel.

As an exemplary embodiment, the area of the smallest section of said packet is at least equal to one half of the area of the section of the microchannel at the location of a first electrode or at the location of a second electrode, whichever is smaller.

The packet may be a spherical droplet with a diameter comparable with the diameter of the microchannel, or an elongated droplet spanning the whole section of the microchannel.

The device according to the present invention may be used to fuse colloids to form a chain, for instance.

The device may also be used for screening processing.

The invention also relates to, according to another of its aspects, a method for displacing at least two packets towards each other in a microchannel, in particular in order to collapse the at least two packets, the microchannel having a longitudinal axis, said method comprising:
 introducing the at least two packets in the microchannel,
 generating an electric field within at least one portion of the microchannel, at least when the packets are located within said microchannel portion, said electric field being preferably substantially collinear to the axis of the microchannel in said portion and having an amplitude and a frequency chosen such as to displace the two packets towards each other.

When the electric field is generated by at least two electrodes axially spaced along the axis of the microchannel, said electrodes being separated by a gap, the method may comprise:
 before generating said electric field, positioning two packets in the gap between the electrodes, said packets being in static equilibrium,
 generating said electric field.

In a variant, the packets for collapsing may be placed initially in a flowing stream such as to perform an in-flight operation of collapsing.

The method may thus comprise:
 positioning two packets in the microchannel, at least one of which being outside the gap between the electrodes,
 displacing the packets towards the gap, for example via a flowing stream in the microchannel,
 generating said electric field at least when the packets are located in the gap.

In an exemplary embodiment of the invention, at least one of said packets contains biological material, for example a cell or a cytoplasm nucleus. The method for collapsing at least two packets is particularly advantageous when the packets contain a biological membrane.

Said method may be carried out in order to form hybridoma or to manipulate embryonic founder cells.

The invention also relates to, according to another of its aspects, a method for displacing at least two packets towards each other in a microchannel, in particular in order to collapse them, or for splitting at least one packet, the microchannel having an axis, said method comprising:
 positioning the at least two packets or the at least one packet in a portion of the microchannel,
 delivering into said portion of the microchannel a solution of a surfactant able to alter the interfacial tension between said at least two packets or said at least one packet and the environment thereof.

The invention also relates to, according to another of its aspects, a method for splitting at least one packet in a microchannel having a longitudinal axis, said method comprising:
 introducing the at least one packet in the microchannel,
 generating an electric field within at least one portion of the microchannel, at least when the at least one packet is located within said at least one portion, said electric field being preferably substantially collinear to the axis of the microchannel in said portion and having an amplitude and a frequency chosen such as to split the packet.

The invention also relates to, according to another of its aspects, a method of monitoring the collapsing of at least two packets or splitting of at least one packet, the method comprising:
 causing collapsing or splitting in a microchannel using the microfluidic device as defined above,
 detecting the collapsing or splitting, for example by using a video device or by measuring an electric parameter such as an electric resistance associated for example with at least one substance contained in the microchannel.

The invention also relates to, according to another of its aspects, a method for displacing at least one packet in a microchannel having an axis, said method comprising:
 introducing at least one packet in the microchannel,
 generating an electric field within at least one portion of the microchannel, at least when the at least one packet is located within said portion, said electric field being preferably collinear to the axis of the microchannel, such as to displace the packet along the microchannel. Said electric field may be continuous.

The operation of displacing at least one packet in the microchannel may be performed independently from an operation of collapsing or splitting.

In a variant, said operation of displacing at least one packet in the microchannel may be carried out in order to position appropriately said at least one packet in the microchannel before performing the operation of collapsing or splitting.

The invention relates to, according to another of its aspects, a method for performing at least one operation on at least one packet in a micro-container, in particular a microchannel, wherein said micro-container has at least one tubular portion defining an internal space of the micro-container, wherein:
  the tubular portion is made of a non internally coated bulk fluorinated material, or
  the tubular portion is made of a bulk non-fluorinated material and is coated on all a circumference of an internal surface of the tubular portion with a permanent layer, or
wherein the micro-container comprises a succession of at least two tubular portions, a first tubular portion made of a bulk fluorinated material and a second tubular portion made of a bulk non-fluorinated material coated on all an inner circumference with a permanent layer,
wherein said permanent layer is preferably hydrophobic, and wherein said micro-container is at least partially filled with a carrier fluid immiscible with said packet and containing at least one surfactant at a concentration large enough to decrease the surface tension between said packet and said carrier fluid.

The expression "bulk material" means a monolithic material.

For instance, a bulk material according to the present invention is different from an assembly of two portions made of the same material, for example of PDMS (polydimethylsiloxane).

A bulk material also differs from an assembly of two portions made of different materials, such as an assembly of a portion made of PDMS bonded to a portion made of glass or an assembly of a portion made of borosilicate to a portion made of silicone.

In such known systems, the difference of chemical nature between different parts of the circumference of the micro-container or microchannel, tends to make interactions of the packet or of the carrier fluid with such parts different, and thus to provide poorer control over the operations performed on said packet.

By "permanent layer", we mean a layer which is not carried onto and removed from the inner surface of the micro-container by the carrier fluid, as would be the case, typically, for a surface-active component added in the fluid, and in particular, surfactants such as SPAN, SDS, Pluronics®, and the like. The use of a permanent layer is advantageous since it is more robust, and it provides more freedom on the composition of said carrier fluid.

In the method according to the present invention, for some applications, one may add to said carrier fluids such surfactants.

A tubular portion may have a circular or non-circular cross-section. For instance, the cross-section may be rectangular.

The cross-section of a tubular portion may vary or not along a length of the micro-container.

The permanent layer may comprise a material selected among: fused silica glass, PDMS (polydimethylsiloxane), PMMA (polymethylmethacrylate), any kind of elastomer or plastic, such as for example polyethylene, polyimide, epoxy, Teflon®, Parylene®, polystyrene, polyethylene terephtalate, polyester, cyclic olefin copolymer, non-conducting oxide such as, for example, glass, silicon dioxide, diamond, non-conductive ceramics, a silicone, an elastomer, a glassy material, a mineral material, a ceramic, a polymer, a thermoplastic polymer, a thermocurable resin, a photocurable resin, a copolymer, a silane, a fluorosilane, a fluoropolymer.

The invention also relates to, according to another of its aspects, a device for performing at least one chemical, physical or biological operation on at least one packet embedded in a carrier fluid immiscible with said packet, said device comprising at least a micro-container surrounding said carrier fluid containing said packet, wherein the inner surface of said micro-container is fluorinated, and said carrier fluid contains a surfactant at a ratio concentration of at least 0.1 cmc (critical micellar concentration).

The micro-container according to the invention can be of any shape. It can for instance be a rectangular section microchannel, a cylindrical microcapillary, a thin slab-like volume, or a cylindrical, pyramidal or rectangular microvial.

For some applications, the device according to the invention can gather more than one, preferably more than 10 or more than 100, and up to several hundred thousands such micro-containers.

In an embodiment, the micro-container has at least one inlet port. The micro-container may have at least one outlet port. Optionally the port(s) can be connected to one or several reservoirs, to one or several pumps, or to one or several sampling devices.

Optionally, the micro-container can also be part of a network of connected microchannels and reservoirs.

The invention also relates to, according to another of its aspects, a method for performing at least one operation on at least one packet in a micro-container, in particular a microchannel, wherein said micro-container has an inner tubular hydrophobic surface, wherein said micro-container is at least partially filled with a carrier fluid immiscible with said packet and containing at least one surfactant at a concentration large enough to decrease the surface tension between said packet and said carrier fluid.

Said operation may be at least one of displacing the at least one packet, splitting the at least one packet, coalescing the at least one packet with at least another packet, reacting the at least one packet.

The displacing may comprise circulating the carrier fluid in the micro-container.

The operation may be carried out in the absence of any electrical field.

The operation may comprise displacing the at least one packet from an inlet of the micro-container towards an outlet of the micro-container.

The operation may comprise exposing successively the at least one packet to at least two different physical and/or chemical conditions, in particular to at least two different temperatures.

The invention also relates to, according to another of its aspects, a microfluidic device comprising a micro-container, in particular a microchannel, having an inner tubular surface, said device further comprising a tubular bulk hydrophobic portion forming an internal space of the micro-container wherein said bulk portion is coated with a hydrophobic layer.

In one embodiment, the bulk portion is made of a fluorinated material. In a variant, the bulk portion is made of a non-fluorinated material and coated with a fluorinated layer.

The microfluidic device may comprise a succession of at least a first and a second bulk portions, the first portion being made of a fluorinated material, without coated layer, and the second portion being made of a non-fluorinated material and coated with a fluorinated layer.

In a variant, the microfluidic device may comprise two portions made of Teflon® assembled together for forming a circumference of the micro-container.

The invention also relates to, according to another of its aspects, a method for performing at least one operation on at least one packet in a micro-container, in particular in a microchannel, said micro-container having an inner surface, wherein said micro-container is filled with a carrier fluid immiscible with said packet and containing at least one surfactant, wherein the difference between the interfacial tension between the packet and the inner wall of the micro-container and the interfacial tension between the packet and the carrier fluid is at least 26 mN/m, preferably at least 35 mN/m. Said difference may be comprised between about 35 mN/m and about 45 mN/m.

In Tice et al., *Langmuir* 2003, 19, 9127-9133, it has been proposed that the transport of droplet by a carrier fluid in a microchannel is performed without interaction with the microchannel wall, if the interfacial tension between said droplet and said carrier fluid is smaller than the interfacial tension between the dropet and the microchannel. In particular, these authors used water droplets, dissolved in a fluorocarbon containing a fluorosurfactant (interfacial tension 12-14 mN/m) in a PDMS microchannel, (interfacial tension 38 mN/m).

In this case, the difference between the droplet/microchannel and the droplet/fluid difference is 24-26 mN/m. Surprisingly, it has been found that in similar conditions, (water droplets in FC40 plus 1H,1H,2H,2H perfluorodecan-1-ol (interfacial tension between this fluid and water 12-20 mN/m, see example 11 and FIG. 14) in a silicone capillary tube (interfacial tension of water to capillary tube: 38 mN/m), this condition (difference of surface tension positive and comprise between 18 and 26 mN/m) is satisfied, however imperfect behavior of droplets, and contamination between droplets (see example 14) are still observed.

In contrast, the silicone is additionally treated with fluorosilane (interfacial tension with water: 55 mN/m), i.e. if the difference between the interfacial tension of the packet with regards to the surface of the microchannel and the interfacial tension between the packet and the fluid is increased to a value comprise between 35 and 45 mN/m, no contamination is observed.

Also, when water droplets are transported in pure FC40 (water/FC 40 interfacial tension: 51.8 mN/m) in a capillary tube of Teflon® (interfacial tension 55 mN/m), the condition stated in Tice et al. is satisfied, and nevertheless unsatisfying droplet transport is observed, and droplet breakage. In contrast, when the droplet/fluid interfacial tension is decreased to a value between 10 and 20 mN/m, by addition of 0.5 to 3% 1H,1H,2H,2H perfluorodecan-1-ol, (difference between the interfacial tension of the packet with regards to the surface of the microchannel and the interfacial tension between the packet and the fluid to a value comprise between 35 and 45 mN/m), irregular droplet motion and contamination can be suppressed.

In a preferred embodiment, the ratio concentration of the surfactant in the carrier fluid is at least 0.1 cmc (critical micellar concentration), preferably at least 0.5, and more preferably 1 cmc.

Advantageously, the concentration of the surfactant in the carrier fluid is comprised between about 0.01% and about 10% w/w (weight by weight), preferably between about 0.1% and about 3%.

In a preferred embodiment, said surfactant is a fluorosurfactant, in particular a fluoroalcohol. In a particular embodiment, the fluorosurfactant is 1H,1H,2H,2H perfluorodecan-1-ol, In one particular embodiment, said bulk portion is made of silicone. For instance, the microchannel is formed by a silicone capillary tube.

In one particular embodiment, the bulk portion is silanized. For instance, the inner surface of the bulk portion is treated with a silane.

In an embodiment, said silane is selected among monomethyl silanes, dimethylsilanes, trimethylsilanes, monochlorosilanes, dichlorosilanes, trichlorosilanes, and the like. In a preferred embodiment, said silane is selected among monomethyl fluorosilanes, dimethylfluorosilanes, trimethylfluorosilanes, monochlorofluorosilanes, dichlorofluorosilanes, trichlorofluorosilanes, and the like. In a yet preferred embodiment, said fluorosilanes are perfluorosilanes. In an embodiment, said silanes have tails with a skeleton involving at least 2 carbon atoms, preferably 4 carbon atoms, yet preferably 8 carbon atoms, and yet preferable 12, 16 carbon atoms or more. In an embodiment, said fluorosilane is selected among 1H,1H,2H,2Hperfluorooctyltrimethylsilane and 1H,1H,2H,2Hperfluorodecyltriethoxysilane (Fluorochem). Said silane is preferably dissolved in a water-free solvent such as ethanol, methanol, octane, DMF, and the like. In another embodiment, said silane is deposited on the surface directly from gas phase, by blowing a water-free carrier gas over the surface of said silane, and then into the microchannel.

In an embodiment, said silanization is performed under argon atmosphere. In another embodiment, said silanization is performed under air atmosphere. Preferably, said atmospheres are water-free, because water tend to hydrolyse the silane and prevent its grafting.

In another embodiment, said inner surface of said microchannel can be activated prior to silanization, by one of several methods known from those skilled in the art. In one embodiment, said activation is a plasma activation. In a preferred embodiment, said activation is performed by flowing an acidic solution in said microchannel. In one embodiment said solution is selected among chlorhydric acid, sulphuric acid, nitric acid, phosphoric acid, florhydric acid.

The invention also relates to, according to another of its aspects, to a connector allowing contamination free transport of at least one packet from at least one microchannel towards another microchannel, said connector being constituted by a bulk material having on all its inner surface a hydrophobic layer, said layer comprising one of a fluorinated material and a silanized material.

In a preferred embodiment, said bulk material is an elastomer.

In a further preferred embodiment, this connector is related to at least one of its inlet(s) or outlet(s), to another microchannel made of a different material, preferably a non-elastomeric material.

In another embodiment, said connector has at least three orifices related by microchannels. Interestingly, also, this connector comprises a portion that can be inserted into a pinch valve or a perisaltic pump, in order to control the flow of fluid inside said connector, between its different orifices.

Said connector can optionally be prepared by first preparing a molded piece, and then connecting to at least one of its orifices an elastomeric tubing, said elastomeric tubing also bearing on its inner surface a hydrophobic layer.

Preferably, and in contrast with most microchannels used in prior art to manipulate packets in microfluidic systems, in the invention, the section of the microchannel(s) is cylindrical: this avoids sharp angles, that tend to retain fluid or solid material, pin contact angles, and thus increase the risk of contamination between packets.

The invention also relates to, according to another of its aspects, a micro-container selected among:
- a micro-container made of a bulk fluorinated material,
- a micro-container made of a bulk non-fluorinated material having a surface covered on all its circumference with a permanent insulating layer,
- and a microchannel comprising at least a portion made of a bulk fluorinated material and at least a portion made of a bulk non-fluorinated material, said portion made of a bulk non-fluorinated material being covered on its all circumference with a permanent insulating layer, said micro-container being at least partially filled with a carrier fluid immiscible with said packet and containing at least one surfactant at a concentration large enough to decrease the surface tension between said packet and said carrier fluid.

The invention relates to, according to another of its aspects, a microfluidic device comprising at least one micro-container, in particular at least one microchannel, and a connector in communication with the micro-container, said connector being configured for connecting said micro-container to at least one of another micro-container, in particular a microchannel, and an inlet or outlet port of the device, wherein said connector has an inner surface comprising at least one hydrophobic layer.

The invention also relates to, according to another of its aspects, a connector configured for being mounted at one end of a capillary tube forming a microchannel, wherein said connector has an inner surface comprising at least one hydrophobic layer.

The invention also relates to, according to another of its aspects, a kit comprising:
- a microfluidic device comprising a microchannel,
- a connector as disclosed above, to be mounted on said microfluidic device.

The invention also relates to, according to another of its aspects, a kit for performing at least an operation on a packet comprising:
- a micro-container, in particular a microchannel, having an inner surface comprising at least one hydrophobic material,
- a carrier fluid immiscible with said packet containing at least one surfactant at a concentration large enough to decrease the surface tension between said packet and said water-immiscible fluid.

The invention also relates to an assembly comprises:
- a connector as disclosed above,
- at least one capillary tube connected to said connector.

The connector may be a T-connector.

Preferably, the capillary tube has a fluorinated or silanized inner surface.

The invention also relates to, according to another of its aspects, a device for performing a PCR comprising:
- a microchannel comprising a coil made of a capillary tube at least partly filled of a fluorosolvent containing a surfactant, the coil comprising a denaturing region, an annealing region and an elongation region exposed to different temperatures.

BRIEF DESCRIPTION OF THE DRAWINGS

The invention may be better understood on reading the following detailed description of non-limiting embodiments, and on examining the accompanying drawings, in which:

FIG. 7 is a diagrammatic view of an electric field distribution in a portion of the microchannel, FIG. 8 is a diagrammatic partial view of a device according to a variant of the invention, and FIGS. 9 to 13 illustrate diagrammatically and partially other variants of the invention.

1: FIRST EXEMPLARY EMBODIMENT OF THE INVENTION

Figure 1:
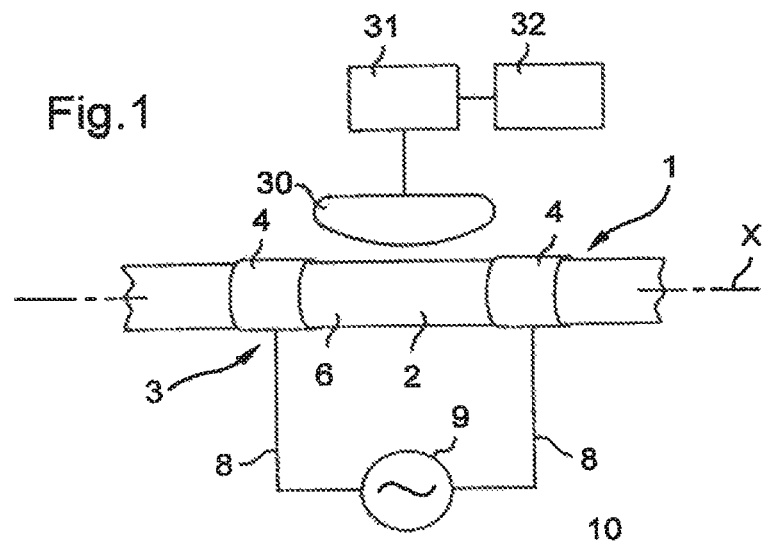
FIG. 1 is a diagrammatic partial view of a microfluidic device according to the invention.

FIG. 1 shows a microfluidic device 1 according to the invention, said device comprising a microchannel 2 and an electrode assembly 3. The microchannel 2 has a longitudinal axis X and an internal cross section that is circular.

The electrode assembly 3 comprises a pair of electrodes 4, each electrode 4 comprising a metal cylinder, for example aluminium. The length of each electrode 4 is for example 4 mm and the inner diameter 1.5 mm and the outer diameter 1.9 mm.

The electrodes 4 are placed around the microchannel 2 and are spaced along the axis X by a gap 6. The electrodes 4 are connected to a generator unit 9 via connection elements 8 comprising electrical wires.

The electrodes 4 are housed in a support 10 comprising two support members 11, each being a substantially rectangular parallelepiped made of Plexiglas®, for example with a width of 24 mm, a height of 20 mm and a depth of 20 mm.

A first cylindrical hole 12, for example of diameter 1.9 mm, is drilled in each support member 11 along the axis X at the center of the support member 11 for holding the electrode 4. The first hole 12 extends from a front face 13 towards a rear face 14 of the support member 11, opposite to the front face 13.

A second hole 17 is drilled perpendicular to the first hole 12 for receiving a connection element 8 connecting the corresponding electrode 4 to the generator unit 9.

Each support member 11 further comprises two holes 20 and 21 whose axes are parallel to the axis of hole 12 and configured for receiving respectively a Teflon® screw 22 and a metal rod 23 in order to maintain the support members 11 assembled with the holes 12 being collinear.

Figure 2:
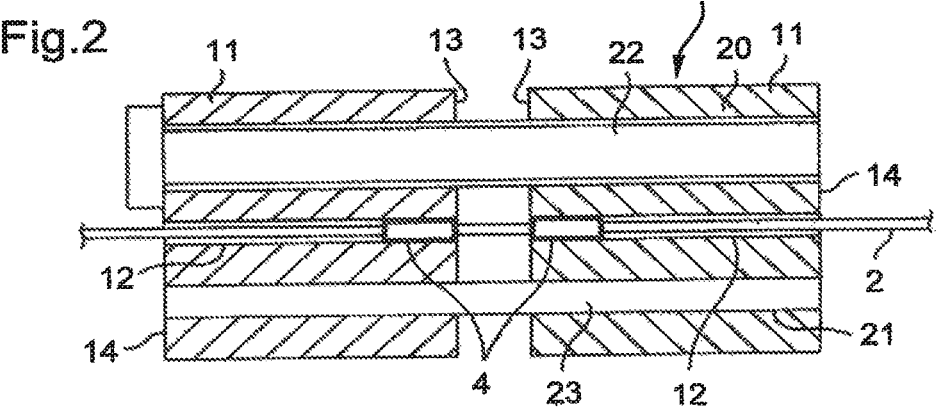
FIG. 2 is a diagrammatic view in cross section of the device of FIG. 1.

Each electrode 4 is mounted in the corresponding support member 11 such that the electrode 4 is flush with the front face 13, as illustrated in FIG. 2.

The front faces 13 of the support members 11 are spaced for example by a length of 2 mm defining a 2 mm gap 6 between the electrodes 4.

The generator unit 9 comprises for example a function generator connected to an amplifier such as to deliver sinusoidal voltages up to 2 kV with frequencies up to 1 kHz. The generator unit 9 may also comprise a central processing unit such as a computer to programmably control the voltage delivered to the electrodes 4.

Figure 3:
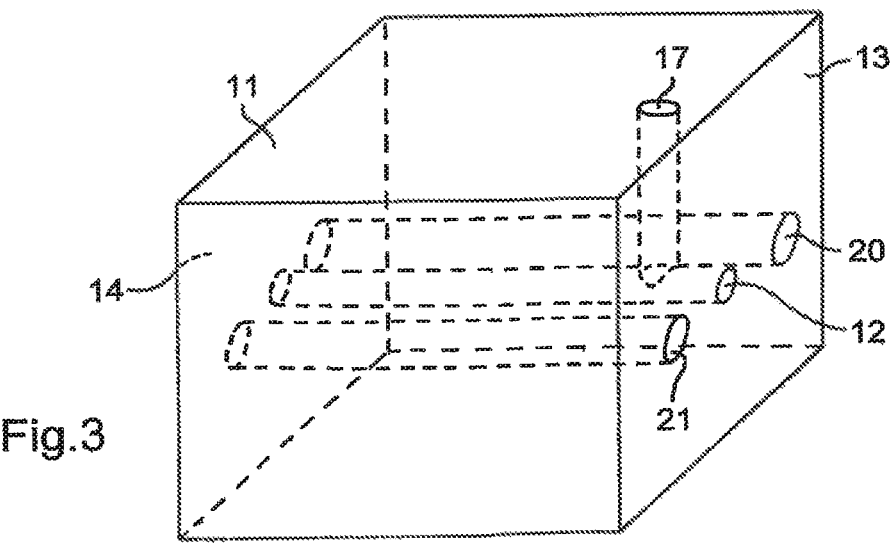
FIG. 3 is a diagrammatic perspective view of a support member of the device of FIG. 2, FIGS. 4A-4C and 5A-5C illustrate diagrammatically respectively three steps of two coalescence operations according to the invention.

FIG. 3 shows diagrammatically the orientation of electric field given by the arrows together with the equipotential lines.

As one can see, the electric field is substantially collinear to the axis X of the microchannel 2 and thus favors electrocoalescence and minimizes any effect of dielectrophoresis.

The device 1 may be mounted on an observation stage of a binocular microscope 30 connected to a CCD camera 31 and a video recorder 32, as illustrated on FIG. 1, thus enabling the monitoring of the collapsing of two packets or the splitting of a packet in the microchannel.

The device may be configured such that after the collapsing or splitting, the packet(s) are drained off.

2: SECOND EXEMPLARY EMBODIMENT OF THE INVENTION

FIG. 8 shows an electrode assembly 3' comprising two composite electrodes 35 each having a pair of substantially parallel equipotential plates 36 facing each other and sandwiching a microchannel 2' which has a rectangular cross-section. Each pair of plates 36 is connected to a respective pole of the generator unit 9.

3: EXAMPLE OF AN OSCILLATION METHOD

In an embodiment, the droplet fluid is TBE 5× buffer (0.45 M Trisbase®, 0.45 M boric acid and 0.01 M EDTA; Sigma®) dyed with 0.25 wt % bromophenol blue for observation in a carrier fluid of fluorinated oil (FC-40, 3M) with 0.5 wt % 1H,1H,2H,2H perfluorodecan-1-ol (Fluorochem®) added to prevent interactions with the wall of the microchannel 2. The droplet conductivity is 3 mS/cm and the carrier fluid conductivity is $2.5.10^{-13}$ mS/cm. For droplet formation, the two fluids are layered in a 1.5 ml Eppendorf® tube so that the bottom layer consists of approximately 0.6 ml of the carrier fluid (FC-40/1H,1H,2H,2H perfluorodecan-1-ol) and the upper layer consists of approximately 0.6 ml of the droplet fluid (TBE 5×/bromophenol blue).

The microchannel 2 is filled from a syringe pump (commercialised by KD Scientific) using for example a Hamilton® Gas-Tight 250 µl syringe filled with the carrier fluid. The excess fluid pumped into the microchannel may be collected in a waste reservoir. After completely filling the capillary, the microchannel 2 is placed into the carrier fluid phase of the layered Eppendorf® tube. The pump is then aspirated at a rate of 1 ml/hr. Droplets are formed by oscillating the microchannel between the carrier phase and the droplet phase, either manually or by attaching the microchannel to a mechanical oscillator, at for example approximately 2 Hz. Droplets formed by this method have approximately the same diameter as the channel.

4: EXEMPLARY METHOD FOR DISPLACING A DROPLET IN A MICROCHANNEL

The method may be carried out with any of the devices defined above.

A single droplet is formed by the oscillation method described above. Using the syringe pump, the droplet is aspirated into the gap 6 between the electrodes 4. When the droplet has reached the section of the gap just before the upstream electrode, the flow is stopped and the system allowed to settle to equilibrium. A continuous voltage is then applied, with the positive voltage applied to the electrode 4 closest to the droplet and with the farthest electrode grounded. The motion of the droplet towards the grounded electrode can be recorded on video and the time for a given displacement measured. The droplet only moves when it is between the electrodes 4 and stops when it is under the grounded electrode.

5: EXAMPLE OF STATIC COALESCENCE

The static coalescence may be performed by any of the devices defined above.

Droplets are formed by the oscillation method described above such that the spacing between the two droplets is larger than the gap 6 between the electrodes 4. A first droplet is initially brought into the gap 6 between the electrodes 4 using the syringe pump. When the droplet arrives at the upstream electrode, the flow is stopped. The droplet is moved against the direction of the previously applied flow using the electric field actuation described above until it reaches the downstream electrode. The flow is restarted until the first droplet returns to the upstream electrode. This procedure is repeated until a second droplet appears between the electrodes 4. The microchannel position in the electrodes is then adjusted so that the second droplet is outside of the gap 6 between the electrodes. The first droplet is moved against the direction of the previously applied flow until the gap between the two droplets is for example 0.5 mm. The microchannel is then repositioned such that the midpoint between the two closest edges of the droplets is centered between the two electrodes and the system is allowed to settle to equilibrium.

Figure 4A:
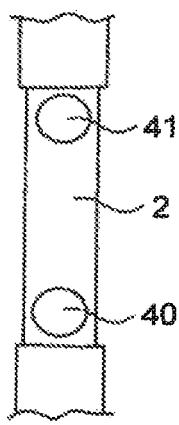
Figure 4B:
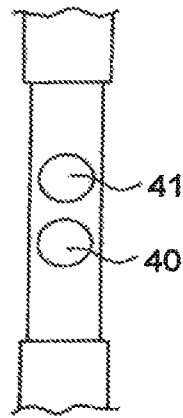
Figure 4C:
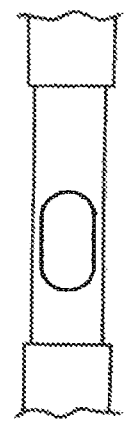

In the example depicted in FIGS. 4A to 4C, the first droplet 40 has a diameter of about 540 μm and the second droplet 41 has a diameter of about 560 μm. Upon applying a 2 kV, 1 kHz sinusoidal voltage to the electrodes 4, initial droplet motion is steady, with the smaller droplet 40 moving at a slightly higher velocity (FIGS. 4A and 4B). When the droplets 40 and 41 come into close contact they rapidly accelerate and drain the intervening film (FIG. 4C), which indicates that the device 1 should provide essentially instantaneous coalescence of droplets which are initially close together, such as occurs after two droplets arrive simultaneously at a T-junction.

6: EXAMPLE OF IN-FLIGHT COALESCENCE

The in-flight coalescence may be performed by any of the devices defined above.

The first droplet 43 may have a diameter of about 580 μm and the second droplet may have a diameter of about 560 μm.

After positioning the droplets, the microchannel is displaced such that both droplets are outside the gap 6 between the electrodes 4. A 2 kV, 1 kHz sinusoidal voltage is then applied to the 2 mm-spaced electrodes and kept on throughout the duration of the experiment. After applying the electric field, the flow is started by aspirating with the syringe pump at 50 μL/hr.

Figure 5A:
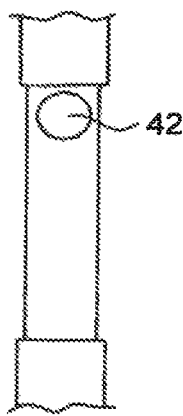
Figure 5B:
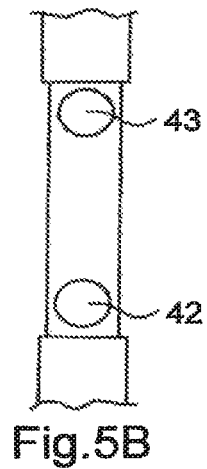
Figure 5C:
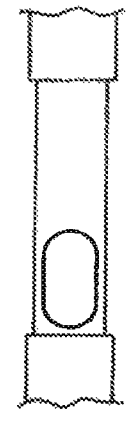

The droplet 42 enters the gap 6 between the electrodes 4 and moves at a constant velocity in the absence of the droplet 43 (FIG. 5A). The leading interface of the droplet 43 appears after 13 sec, but has no effect on the droplet 42. Only when the trailing droplet is well inside the gap 6 between the electrodes does the dipolar force manifest itself. Thereafter, the coalescence time is essentially the same as in the static case (approximately 8 sec) for these widely separated droplets, but the dynamics are slightly different due to the flow. The dipolar force is sufficiently strong to stop the droplet 42 (FIG. 5B), whereupon the droplet 43 moves toward it at a constant rate, closing the distance at essentially the same rate as in the static case. Once the droplets are close together, the strong dipolar force rapidly drains the intervening fluid and coalescence is achieved (FIG. 5C).

7: EXAMPLE OF DROPLET SPLITTING

Figure 6A:
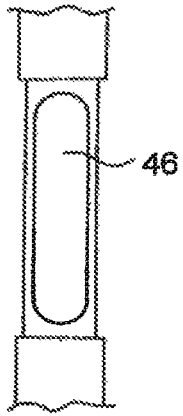
FIGS. 6A-6C illustrate diagrammatically and partially three steps of the aliquoting of a droplet according to the invention.
Figure 6B:
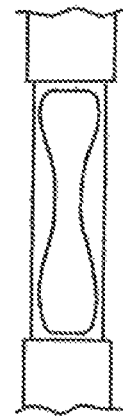
Figure 6C:
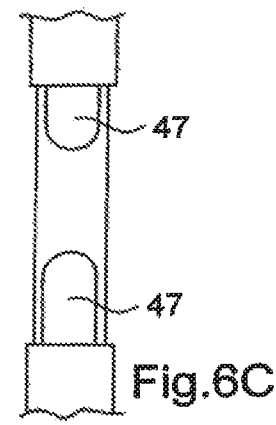
Figure 14:
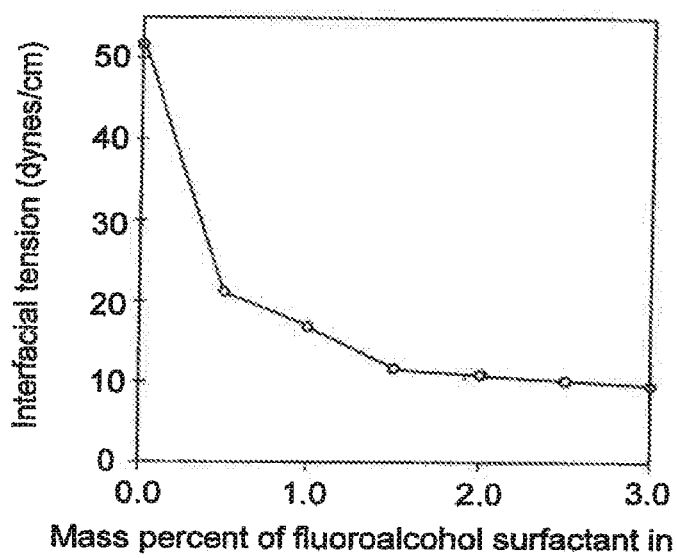
FIG. 14 plots the interfacial tension between fluorosurfactant 1H,1H,2H,2H perfluorodecan-1-ol and fluorinated oil FC-40, as measured in example 11.

A single large droplet 46 is formed by oscillating the interface as described above but at a lower frequency. The droplet 46 is brought into the gap 6 between the electrodes, by aspirating with the syringe pump (FIG. 6A). The drop depicted in the present embodiment is an ellipsoid of revolution with a 2.5 mm long axis. Upon applying a 2 kV, 0.1 Hz square tension, the drop 46 splits into two smaller, stable drops 47 (FIGS. 6B and 6C) that are ejected from the gap 6.

Typical operating conditions for achieving a clean droplet splitting, that is to say one big droplet splitting into two smaller and stable ones without formation of any satellite drops may consist in a square voltage with a frequency between 0.1 and 1 Hz and an amplitude between 1 kV and 2 kV. Under such condition, the droplet may break in less than 1 minute. The lowest the voltage applied, the "cleanest" the splitting but the longer it may take. The droplet length may be about the length of gap 6.

8: OTHER EXEMPLARY EMBODIMENTS OF THE INVENTION

As illustrated in FIGS. 9 and 10, the microchannel portion 50 between the electrodes 4 may form a T-intersection with a transverse channel 51. After coalescence of the droplets caused by the electric field between the electrodes 4, the resulting droplet 52 may be driven in the transverse channel 51, for example by using a syringe pump connected to the transverse channel 51.

As illustrated in FIGS. 11 and 12, the droplet splitting may be performed by extracting a droplet 53 from a relatively large mass of fluid 54 by applying the electric field between the two electrodes 4.

Thus droplets 53 can be formed when desired, for example by programmably controlling the electrodes 4.

9: ANOTHER EXEMPLARY EMBODIMENT OF THE INVENTION

FIG. 13 shows a device 60 according to the invention, said device 60 comprising a microchannel 61 connected in a portion 62 to first and second side channels 63 and 64.

Portion 62 may for instance be situated substantially at the middle of the microchannel.

In the present embodiment, the microchannel 61 may have a thickness of about 100 μm and a width of about 300 μm and the side channel 63 a thickness of about 100 μm and a width of about 50 μm.

The side channel 63 is connected to a delivery system 66 comprising a syringe pump having a reservoir 67 containing a solution of surfactant of oleic acid and SDS in hexadecane, at a concentration superior to the critical micellar concentration.

The microchannel 61 is filled with a solution containing hexadecane containing SPAN® 80 at a concentration adjusted to avoid interaction of aqueous droplets with the microchannel walls.

The side channel 64 is connected to a sprInge pump 68 in aspiration mode configured to aspirate the solution from the microchannel 61.

Two droplets 70 of a 5×TBE Buffer are introduced and displaced in the microchannel 61 by its both ends. The aspiration of droplets 70 by both ends is synchronized so that the droplets 70 arrive from both sides at the same time at the portion 62. When the droplets 70 are in the portion 62, a solution of surfactant contained in the reservoir 67 is delivered by the delivery system 66 into the portion 62 of the microchannel with a predetermined flow rate such as droplets 70 coalesce. The optimal flow rate may be determined by progressively increasing the flow until droplets coalesce at each collision, which sets the optimal flow rate.

In another embodiment, the solution of surfactant may be delivered in pulses synchronized with the arrival of the pair of droplets at the connection portion 62.

The resulting droplet 71 is collected in syringe pump 68 for further use, or e.g. transferred to another microchannel for detection.

10: EXAMPLE OF FORMATION AND TRANSPORTATION OF REGULAR ARRAYS OF WATER DROPLETS IN A FLUORINATED OIL CONTAINED IN A FLUOROPOLYMER CAPILLARY TUBE

Trains of droplets are created by using a Y-connector (Upchurch Scientific) connected to an electro-pinch valve (NResearch, Caldwell N.J.). One entry to the Y-connector was filled with TBE 5× buffer (0.45M Trisbase, 0.45M boric acid, and 0.01M EDTA, Sigma) dyed with 0.25 wt % bromophenol blue for ease of observation. The other side of the Y-connector and the test capillary (PFA, i.d. 800 µm, Upchurch Scientific) were primed with either the bulk fluorinated oil FC-40 (3M) or FC-40 containing various amounts of a fluoroalcohol surfactant (1H,1H,2H,2H perfluorodecan-1-ol, Fluorochem). Droplet trains were created by cycling the electrovalve with a LabView program while aspirating with a computer-controlled Harvard milliliter module syringe pump. A typical cycle consists of 6 seconds of aspiration from the TBE line and 8 seconds of aspiration from the FC-40 line. The droplets were observed with a binocular microscope (Olympus) and recorded using a CCD camera (Hitachi) and WinTV.

The stability of droplet trains in the fluidic system is first tested. In previous work on segmented flow PCR, cross-contamination between droplets was attributed to droplet instability and the formation of small satellite droplets. We not only wanted to look for droplet breakage in individual droplets, but also to observe the overall stability of droplet trains containing several hundred droplets. The stability of such trains is essential for high-throughput applications of our technique.

When the droplets are entrained in pure FC-40, it has been observed that they occasionally stick to the walls. This is unexpected, since both the walls and the carrier fluid are fluorinated, and it has been expected that the walls will be strongly wetted by the FC-40. The sticking has been attributed to imperfections (either roughness or chemical inhomogeneities) in the capillary walls, which would be expected in bulk capillaries manufactured by an extrusion process. The layer of FC-40 between the droplets and the capillary wall is very thin, and small perturbations to the wall surface could disrupt the lubrication flow. In any event, once one droplet becomes entrained on the wall, even temporarily, the train as a whole loses its stability. The trailing droplet collides with the entrained droplet and exchanges fluid, the entrained droplet is released from the wall, and the trailing droplet becomes entrained. This process proceeds ad infinitum and would be catastrophic in any PCR application.

The fluoroalcohol surfactant is then added to FC-40 in the range of 0.5-3.0 wt %. Upon making trains containing over 200 droplets, no transient pinning to the walls, satellite droplet formation, or instabilities in the droplet train are observed.

11: MEASUREMENT OF INTERFACIAL TENSION BETWEEN A WATER DROPLET AND A SOLVENT CONTAINING FLUOROSURFACTANT

Interfacial tension measurements were made using a homemade drop-volume tensiometer. The FC-40/surfactant drop is dispensed into a reservoir of TBE 5× buffer from a 0.8 mm ID Teflon® capillary tube. Using a 50 µL Hamilton gastight syringe and a Hamilton PSD/2 syringe pump at maximum resolution, the drop volume could be increased in 25 nL increments with arbitrary waiting times between steps. To allow for equilibration of the surfactant, we typically waited 30 seconds between steps. The tension measurements are the average of at least 15 different drops, corrected for wetting of the Teflon® tip.

12: EXAMPLE OF PCR AMPLIFICATION OF DNA IN A DEVICE ACCORDING TO THE INVENTION, INVOLVING A CHANNEL MADE OF BULK FLUOROPOLYMER

Figure 15:
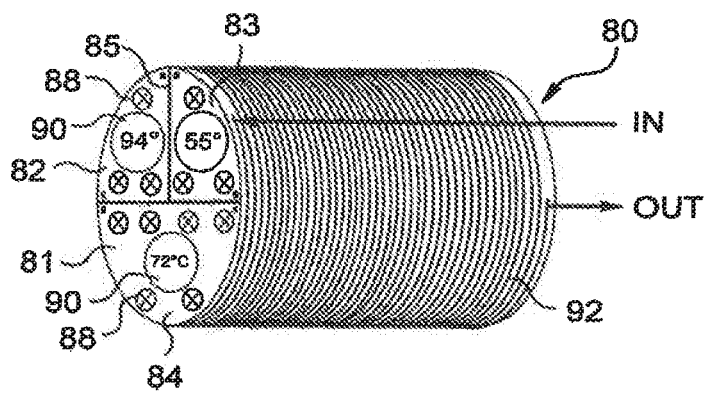
FIG. 15 illustrates diagrammatically and partially a cycling PCR system used in examples 12 and 13 to amplify DNA in segmented flow according to the invention.

A PCR device 80 is depicted in FIG. 15, said device 80 comprising a 4 cm diameter copper cylinder 81 machined into three pieces corresponding to the denaturing 82, annealing 83, and elongation 84 regions. The elongation region 84 is twice the size of the other two regions, thus occupying half the cylinder 81. The three regions are isolated one from another by polycarbonate sheets 85, which are affixed between the pieces of the copper cylinder. The two ends of the heater are capped with a polycarbonate cylinder to provide structural stability while maintaining isolation between the two zones. Three small holes 88 per quarter cylinder are drilled through the entire device to provide vents for air cooling. Two small holes 89 (for the thermocouples) and one larger central hole 90 (for the heater) are drilled partially through the cylinder in each temperature region. The heating and thermocouple holes are not open to the air-cooling side of the heater. Each region is covered with a thin layer of aluminum foil in contact with the respective region of the copper cylinder to provide heating from above. The foil layers are covered by a polycarbonate shell and a layer of cotton, thereby insulating the cylinder and providing a uniform temperature across the capillary. A small turbine blows ambient air through the three ventilation holes per quarter-cylinder, allowing for better temperature control and uniformity.

Each region includes a resistance heater and two Pt-100 thermocouples. The resistance heaters are located in the center of their respective zone, while the thermocouples are located near the interface between zones. The heating elements and thermocouples are connected to custom electronics. The thermocouples communicate with a custom PID program control written in LabView via a Keithley 2701 multimeter. The temperature of each zone can be set arbitrarily. For the experiments discussed here, it has been used a denaturing temperature of 94° C., an annealing temperature of 55.5° C., and an elongation temperature of 72° C. With our design, a temperature difference of ±0.2° C. across each zone is achieved.

A 4.5 meter long transparent PFA capillary tube 92 (i.d. 800 µm, Upchurch Scientific) enters the cylinder through a groove in the denaturing region, providing an initial denaturation step of approximately 1 minute. The capillary is then wound 35 times around the cylinder, corresponding to 35 PCR cycles. The capillary exits the heater through a hole in the extension segment, providing approximately 30 seconds of additional extension on the $35^{th}$ cycle.

PCR Amplification: The template is a 2823 base pair DNA fragment of Litmus 28i (New England Biolabs). This fragment is amplified on 572 base pairs from base 2008 to base 2580 using Eurogentec primers (lower primer 5'-CGC-ATT-GCG-GTA-TCT-AGA-ACC-GGT-GAC-GTC-3' (SEQ ID NO: 1), upper primer 5'-AGC-TTG-GAG-CGA-ACG-ACC-3' (SEQ ID NO: 2), Eurogentech Oligold). A 50 µL PCR mix is prepared using the Ready Mix Taq reaction mixture (Sigma) according to the manufacturer's specifications with the maximum concentration of template and primers.

The carrier fluid is a bulk fluorinated oil FC-40 (3M) containing 0.5%-1.0% wt. Fluoroalcohol surfactant (1H,1H, 2H,2H perfluorodecan-1-ol, Fluorochem). The surfactant prevents the transient adsorption of droplets to the capillary walls. The 2 µL aqueous droplets are injected into the inlet by aspirating from the capillary outlet using a Hamilton PSD/2 pump and a 100 µL Hamilton gastight syringe. The drops are separated one from another by a 5 µL FC-40 spacer. After injecting the desired number of droplets, the outlet is disconnected from the Hamilton pump and the inlet is then connected to a computer-controlled Harvard milliliter-module pump with a 5 mL Hamilton gastight syringe. The droplets are circulated at 0.1 cm/s.

The droplets are collected at the outlet and analyzed by gel electrophoresis on a 1 wt. % agarose gel in 0.5×TAE buffer. A control amplification sample is made by amplifying the remaining volume of the 50 µL PCR mix in a classic PCR thermal cycler (Perkin Elmer) with a cycle of 1 minute at 94° C., followed by 35 cycles of 94° C. for 30 seconds, 55° C. for 30 seconds, and 72° C. for 1 minute. This mimics the cycling in our continuous-flow PCR, although the lag time for heating and cooling the classic cycler means that the total amplification is approximately twice as long as our flow device. A 2 µL aliquot of the amplified control system is used for the gel electrophoresis.

Figure 16:
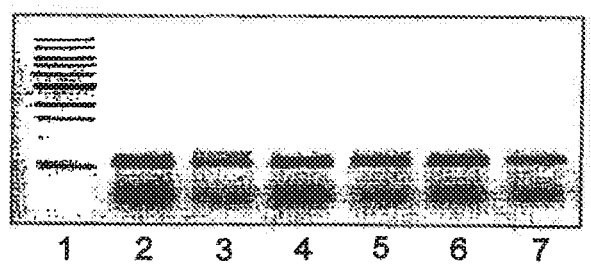
FIG. 16 is a gel electrophoresis of the product of amplification in a train of droplets, as described in example 12.

It has been made a train of five droplets, each one containing the PCR mix and template. The result of this successful amplification in all droplets is depicted in FIG. 16. Lane 1: 1 kbp DNA ladder (New England Biolabs), Lane 2: 24, control sample of mix with DNA, Lanes 3: Droplet 1, Lane 4: Droplet 2, Lane 5: Droplet 3, Lane 6: Droplet 4, Lane 7: Droplet 5.

The degree of amplification in the device according to the invention (lanes 3 to 7) is comparable to that obtained in the conventional thermal cycler (lane 2).

EXAMPLE 13: STUDY OF CONTAMINATION BETWEEN DROPLETS IN A CHANNEL MADE OF BULK FLUOROPOLYMER

Figure 17:
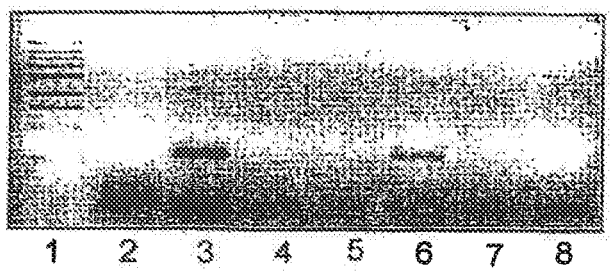
FIG. 17 is a verification of the absence of contamination between neighboring droplets, as described in example 13.

The system has been tested for cross contamination between droplets. All conditions are identical to Example 12, except that two separate PCR mixes are made; a first mix contains the template, primers and Ready Mix reaction mixture and the second mix is identical except that it does not have any template. Five droplets are aspirated, but only the third droplet contains the template. In order to avoid contamination from the tip itself, the latter has been washed it in distilled water between each droplet injection. FIG. 17 shows the gel electrophoresis result from this experiment. Lane 1: 1 kbp DNA ladder (New England Biolabs), Lane 2: 5 µL control sample of mix without DNA, Lane 3: 2 µL control sample of mix with DNA, Lane 4: Droplet 1 (no template), Lane 5: Droplet 2 (no template), Lane 6: Droplet 3 (with template), Lane 7: Droplet 4 (no template), Lane 8: Droplet 5 (no template). There is no observable contamination between different droplets—the only droplet exhibiting any DNA amplification is the third droplet, which contained the DNA.

EXAMPLE 14: EXAMPLES OF DROPLET TRANSPORT IN A CHANNEL MADE OF A NON-FLUORINATED MATERIAL WITH AND WITHOUT COATING WITH A LAYER OF FLUORINATED MATERIAL

In this series of example, the microchannel is made of Silicon tubes (inner diameter 0.8 mm) commercialized by Cole Parmer. The carrier fluid is FC-40 (3M), and the droplets are made of the aqueous buffer TBE 5×. In all cases, a train of droplets is created following the same protocol as described in Example 13, and the shape and migration of droplets in the tube is directly observed and photographed with a binocular and CCD camera.

14A: DROPLETS OF TBE IN PURE FC40 IN UNTREATED SILICONE TUBE

Figure 18A:
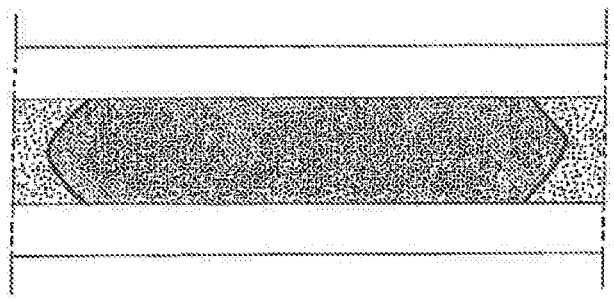
FIGS. 18A-18E show droplet shapes in an untreated, unwashed silicone capillary, with FC40 as a carrier fluid (a) Initial droplet, (b) Later droplet (>$60^{th}$ droplet in the train); with fluorosurfactant solutions at different concentrations (c) 0.15 wt % fluorosurfactant, (d) 0.5 wt % fluorosurfactant, (e) 3.0 wt % fluorosurfactant (examples 14A and 14 B)
Figure 18B:
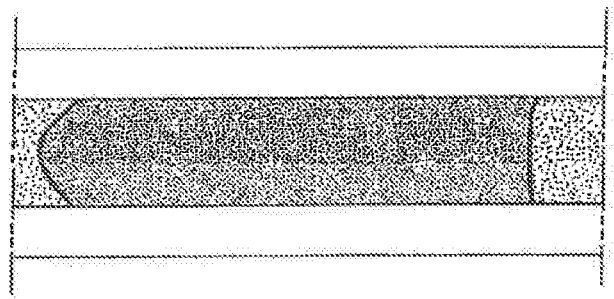
Figure 18C:
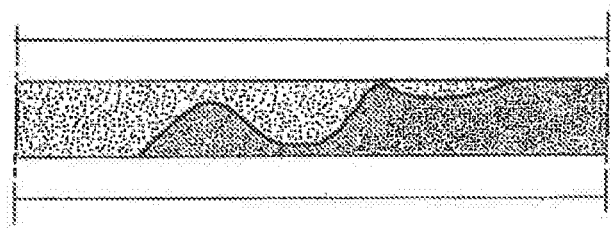
Figure 18D:
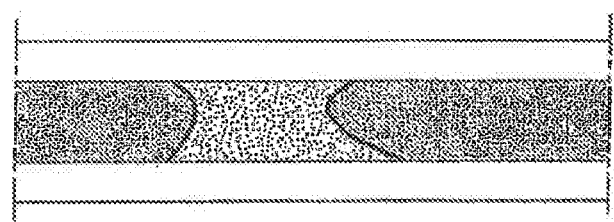
Figure 18E:
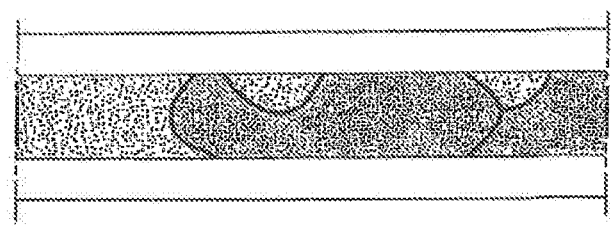
Figure 19A:
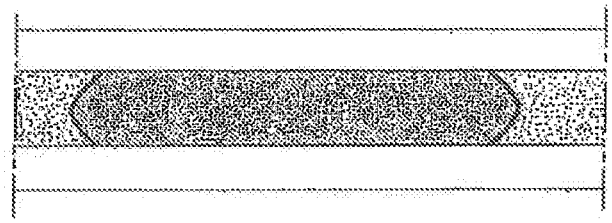
FIGS. 19A-19E show droplet shapes in silicon tubes silinazed in an Argon atmosphere, (a) 7.5 vol % silane, (b) 5 vol % silane, initial droplets, (c) 5 vol % silane, later droplets (>$100^{th}$ droplet), (d) 1 vol % silane, (e) 0.25 vol % silane (example 14C)
Figure 19B:
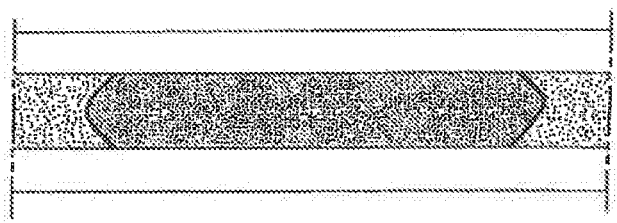
Figure 19C:
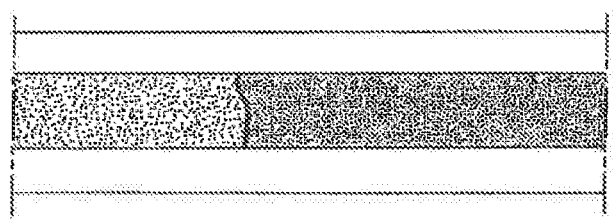
Figure 19D:
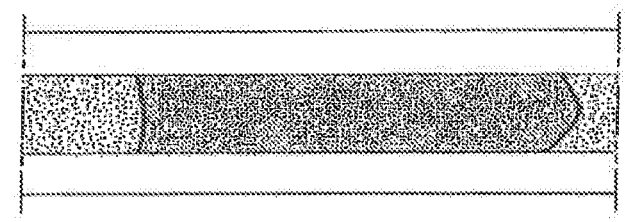
Figure 19E:
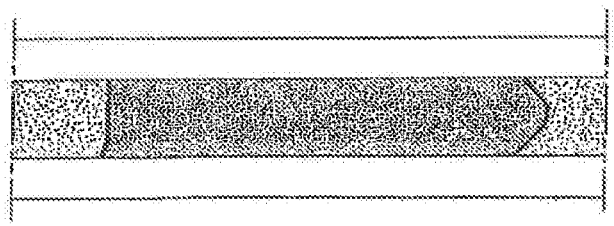

In some instances, the droplets appeared to have a spheroidal shape (FIG. 18a) which indicates that the walls were not wetting. However, after forming a droplet train with several hundred droplets, the walls became wetting at some point during the train (FIG. 18b). In some instances, the first droplets looked like FIG. 1b. It has been presumed that the initially non-wetting behavior observed in some instances is due to a residual product from the manufacturing process. As many droplets are moved through the system, this unknown product is removed from the walls. To test this hypothesis, the tubes are washed with 5 volumes of distilled, purified water. Afterwards, the first droplets always have a behavior like FIG. 18b. For all subsequent experiments, the tubes are always with 5 volumes of distilled, purified water to remove any variations in the initial conditions.

14B: DROPLETS OF TBE IN FC40 WITH FLUOROSURFACTANT ADDED, IN UNTREATED SILICONE TUBE

The behavior of the droplets is tested with the addition of various wt % of a fluorosurfactant, 1H,1H,2H,2H perfluorodecan-1-ol, Fluorochem. The surfactant reduces the interfacial tension between the droplets and FC-40 but does not affect the solid-liquid tension. As a result, the droplets are destabilized and break into many small droplets (FIG. 18 c, d, e) The nature of the breakup depends on the surfactant concentration but even at extremely low levels of fluorosurfactant the droplets are still unstable.

14C: DROPLETS OF TBE IN FC40 WITHOUT FLUOROSURFACTANT ADDED, IN A SILICONE TUBE. TREATED BY SILANIZATION IN ARGON ATMOSPHERE

The tubes were silanized while isolated in an Argon atmosphere. A small quantity of 1N HCl (Sigma) was heated to approximately 60 C on a hotplate. One end of a cleaned silicon tube was connected to a syringe of at least double the volume of the tube and the other end was placed in the warm HCl solution. The HCl was aspirated into the tube until the syringe was partially filled. The HCl was left in the tubes for 5 minutes, during which we occasionally oscillated the syringe pump to provide local mixing. The HCl was then evacuated from the tube and the tube was dried with a flow of Argon. We then connected a new syringe to one end of the tube and placed the other end of the tube in a solution of fluorosilane and spectroscopic grade methanol (Sigma). The fluorosilane is usually 1H,1H,2H,2H,-perfluorooctyltrimethylsilane (Fluorochem). 1H,1H,2H,2H-perfluorodecyltriethoxysilane (Fluorochem) has also been tested and essentially the same results are achieved. All the results shown here are for 1H,1H,2H,2H,-perfluorooctyltrimethylsilane (Fluorochem), which we chose to use because it is less expensive. The silane solution is aspirated into the tube and left for 5 minutes, during which we occasionally oscillated the syringe pump to provide local mixing. The silane solution was evacuated from the tube and the tube was dried with a flow of Argon. The dried tube was then placed in an oven at 110 C for approximately 20 minutes to fix the silanes. The tube was then washed with several volumes of methanol and FC-40 before performing the droplet test.

The results of droplets in Argon-silanized tubes are shown in FIG. 19. For vol % greater than 7.5, we observed no pinning for trains including at least 200 droplets. At 5 vol %, the droplets appeared to be initially nonwetting, but eventually pinned to the wall. For lower vol %, the droplets always wetted the wall. We concluded that 7.5 vol % fluorosilane is necessary to form a stable, nonwetting surface when the reaction is performed under Argon.

14D: DROPLETS OF TBE IN FC40 WITHOUT FLUOROSURFACTANT ADDED, IN A SILICONE TUBE. TREATED BY SILANIZATION IN AIR ATMOSPHERE

To simplify the silanization procedure, the tubes are silanized in air. In order to better preserve the pure silane, the silane/methanol mixture is first performed in Argon but the remainder of the reaction is then performed in a hood using essentially the same protocol as above. The vol % of silane and the time that the silane was allowed to react with the tube (reaction time) are varied. In one instance, the HCl activation step is replaced with plasma activation.

Figure 20A:
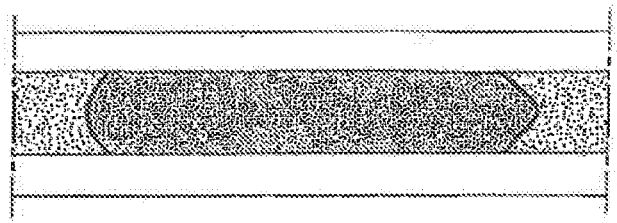
FIGS. 20A-20E show droplet shapes in tubes silanized in air, (a) 10 vol % silane, 5 minute reaction, (b) 7.5 vol % silane, 5 minute reaction, later droplet shape (>110th droplet in train), (c) 5 vol % silane, 30 minute reaction, HCl activation, (d) 5 vol % silane, 30 minute reaction, plasma activation (e) 2.5 vol % silane, 30 minute reaction (Example 14 D)
Figure 20B:
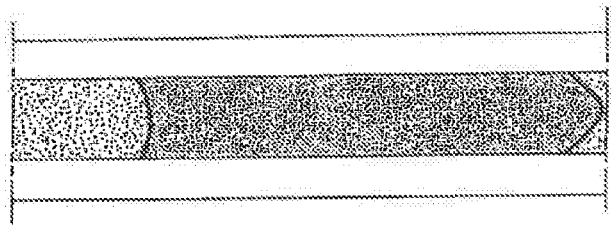
Figure 20C:
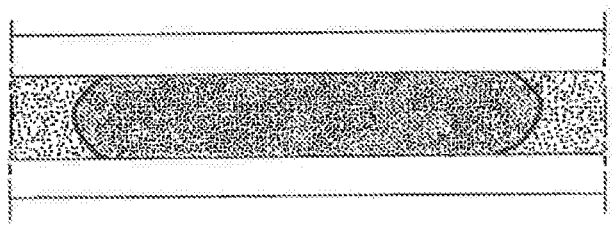
Figure 20D:
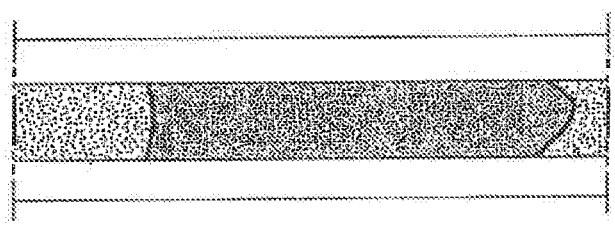
Figure 20E:
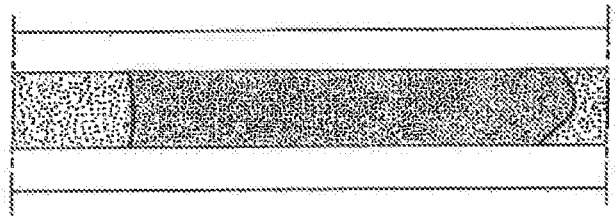

For a 10 vol % silane and 5 minute reaction time, the silanization in air was indistinguishable from the case in Argon (FIG. 20a). At 7.5 vol % silane and a 5 minute reaction, the droplets initially appeared nonwetting but eventually wet the walls (FIG. 20b). It has been found that at 5 vol % silane the droplets still wet the walls, but when the reaction time is increased to 30 minutes, the droplets were nonwetting throughout the entire train (>200 droplets, FIG. 20c). The same parameters (5 vol % silane, 30 minute reaction) are tested but the tube is placed in plasma for 1 minute rather than filling it with HCl. As in FIG. 20d, the plasma activation did not result in a nonwetting surface. Since the plasma must diffuse through the tube for activation, it is less efficient than the liquid activation by HCl, which can be pumped through the tube. It has been tested further lowering the silane concentration to 2.5 vol % silane while retaining the 30 minute reaction time. As in FIG. 20e, the walls are slightly wetting.

The silanization in air probably produces a less uniform coating on the surface than in Argon, since the water in air competes with the silane for the activated surface sites. In essence, the air silanization does not reduce the water-solid tension as much as the Argon silanization. However, the air protocol is much simpler to perform and more amenable to automation.

14E: DROPLETS OF TBE IN FC40 WITH FLUOROSURFACTANT ADDED, IN A SILICONE TUBE. TREATED BY SILANIZATION IN AIR ATMOSPHERE

Figure 21A:
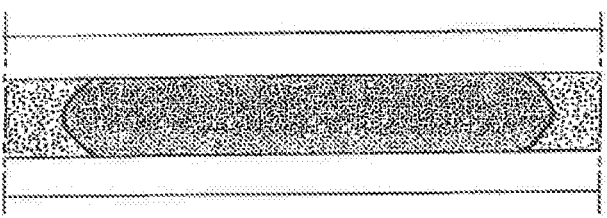
FIGS. 21A-21B show droplet shapes in silanized silicon tubes with 0.5 wt % fluorosurfactant (a) 2.5 vol % silane, 30 minute reaction, 200th drop, (b) 5 vol % silane, 30 minute reaction, 200th drop (Example 14E)
Figure 21B:
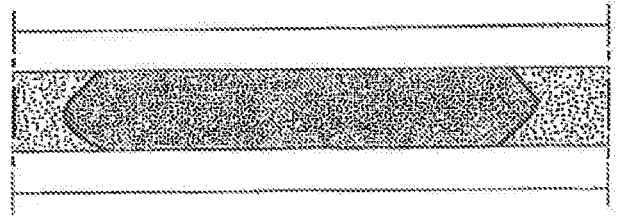

It has been checked if fluorosurfactants, which strongly reduce the FC-40/water interfacial tension, are sufficient to overcome the nonuniformities (and concomitantly lower water-solid tension) that arises from the air-silanized surface. As indicated in FIG. 21, a small concentration of surfactant (0.5 wt %) is sufficient to prevent wetting at both 2.5 vol % silane and 5 vol % silane, even after forming a train of 200 drops.

EXAMPLE 15: VERIFICATION BY QUANTITATIVE PCR, OF CONTAMINATION BY DNA BETWEEN DROPLETS TRANSPORTED IN DEVICES ACCORDING TO THE INVENTION PREPARED IN EXAMPLE 14

To test whether unpinned droplet shapes do not lead to contamination, a set of experiments has been performed using quantitative PCR to make a sensitive test of the DNA concentrations in different droplets.

The tubes were prepared according to one of these protocols:
1. No Silane: Tubes were washed with several volumes of distilled water only. Carrier fluid is FC-40 (3M), prepared according to Example 14A.
2. Silane: Tubes were washed and then silanized in air according to the protocol in Example 14D with 5 vol % silane and 30 minute reaction time. The carrier fluid is FC-40.
3. Silane+Surfactant: Tubes were washed and then silanized in air according to the protocol in Example 14E. The carrier fluid is FC-40 with 0.5 wt % 1H,1H,2H,2H perfluorodecan-1-ol.
4. Bulk fluoropolymer+Surfactant. A train of droplets is prepared according to example 13: Teflon capillaries were used as supplied by the manufacturer. The carrier fluid is FC-40 with 0.5 wt % 1H,1H,2H,2H perfluorodecan-1-ol.

One end of the tube was connected to a Y-connector, and the outlets of the Y-connector were selected using an electro pinch valve. One outlet goes to a Harvard millilitre module syringe pump and a 5 ml Hamilton gastight syringe and the second outlet goes to a Hamilton PSD/2 syringe pump with a 100 µl Hamilton gastight syringe. The Hamilton PSD/2 was used to make all of the droplets (by aspiration) or dispense the droplets from the tube (by pumping). The Hamilton millilitre module was used for droplet oscillation inside the tube. Prior to each experiment, the capillary was filled completely with the carrier fluid and the open end was placed in a reservoir of carrier fluid.

The droplets are mixtures of Taqman PCR mix for quantitative PCR containing Gold Taq polymerase enzyme (Applied Biosystems), qPCR Core Reagent Kit (Eurogentec), specific primers, and a fluorescent probe (3'-ATCTGCTG-CATCTGCTTGGAGCCCA-5' (SEQ ID NO: 3), Applied Biosystems). "Mix" samples contained all of the components for PCR except for the template. The "DNA" samples contain cDNA isolated from cell line A549 at a concentration of 6.25 ng/µl. The fragment is amplified on 149 bp corresponding to the RPLPO gene using Proligo primers (upper primer 3'-GGCGACCTGGAAGTCCAACT-5' (SEQ ID NO: 4); lower primer 3'-CCATCAGCAC-CACAGCCTTC-5' (SEQ ID NO: 5)). We made two reservoirs for each experiment, one reservoir with sufficient mix for each control droplet (typically 30 µl) and a second reservoir with sufficient mix and template for the cDNA droplets (typically 22 µl).

It has been tested for contamination during injection by the following procedure. 2 µl has been aspirated from the DNA reservoir and then 4 µl from the carrier fluid reservoir. The tip was then washed by dipping it in a reservoir of distilled water and drying with a ChemWipe. The subsequent 5 drops were formed by aspirating 2 µl from the mix reservoir and 4 µl from the carrier fluid reservoir. After all of the droplets were formed, we reversed the procedure and collected each droplet in a separate Eppendorf tube. The eppendorf tubes were stored at −80 C prior to the quantitative PCR.

The contents of each drop were analyzed by quantitative PCR on a Taqman 7700 qPCR machine (Applied Biosystems). In these experiments, a value of 35 indicates that there was no detectable amount of cDNA in the droplets (i.e. 35 cycles of amplification without a fluorescence signal above the noise threshold), and each integer increment corresponds to a halving in the mass of cDNA.

Table 1 presents the results from the inlet contamination experiment. There was significant contamination in the untreated capillary, as would be expected from the droplet shape. There was also contamination in the silanized capillary. However, there was no contamination in the mix reservoir, so we could conclude that the contamination occurs from droplet transport inside the capillary. For the silanized capillary with fluorosurfactant, we observed some contamination in the first wash droplet and equivalent contamination in the mix reservoir. This led us to believe that the contamination occurred at the tip during transfer, and that more vigorous washing of the tip after the aspiration of the DNA droplet should be sufficient to eliminate contamination at the inlet using a silanized capillary and fluorosurfacant. There was no contamination using the Teflon tip.

We then tested the ability of the fluorosurfactant and silanized capillary to prevent contamination while the droplets were in transit. Using essentially the same aspiration procedure as above with the fluorosurfactant and a silanized capillary, we first made two mix droplets, then a cDNA drop, and then two mix droplets. The difference between the present injection protocol and the one above is that we now washed the tip in two separate distilled water reservoirs after injecting the DNA drop, with the aim of reducing the contamination at the tip. At the end of the procedure we had a 2 μl cDNA drop with two 2 μl mix droplets on either side of it (Control 1 and 2 leading, Control 3 and 4 trailing), where each droplet was spaced by 4 μl of the carrier fluid.

We then aspirated using the Harvard millilitre module so that the droplets were in a straight section of the capillary positioned below an Olympus binocular microscope. Using computer control, we oscillated the Harvard millilitre module so that it pulled the droplets 5 cm in the capillary at an average velocity of 1 mm/sec, and then pushed the droplets 5 cm at an average velocity of 1 mm/sec, so that a single cycle resulted in no net displacement of the droplets. We performed 50 such cycles, so that the total distance travelled by the droplets (5 m) is comparable to that required in our continuous flow PCR machine. By oscillating the droplets, rather than pushing them at a constant rate through a 5 m capillary, we simulate the conditions in a high throughput operation. We occasionally observed the droplets with the microscope to ensure that they were not wetting the walls.

After completing the 50 cycles, we collected the droplets in individual eppindorf capillaries. After ejecting each droplet, we aspirated a 2 μl wash droplet of distilled water to clean the tip. The wash droplets were also collected. All of the droplets and the mix reservoir were analyzed by quantitative PCR as above.

Table 2 presents the results of the quantitative PCR. There was no detectable contamination in any of the control drops. Moreover, there was no detectable contamination in the wash droplets. There was some contamination in the mix reservoir, but this did not lead to contamination in any of the control droplets. We conclude that the combination of the fluorosurfactant and a silanized capillary should be sufficient to prevent contamination in high throughput applications.

We performed essentially the same oscillation experiment using a Teflon capillary and fluorosurfactant. The only difference is that in this experiment we did not wash the tip when collecting the droplets or use the extra wash droplets.

The results with a Teflon tube and fluorosurfactant are presented in Table 3. As in the inlet contamination test, there is no contamination in the mix, indicating that the washing is sufficient to remove the DNA from the tip. There is some contamination in drop 2. We believe that this contamination is due to not washing the tip when collecting the droplets. Drop 2 exits the system immediately after the cDNA drop. It is possible that a small part of the cDNA drop may have become entrained on an imperfection in the tip surface, which would then be transferred to Drop 2. An automated droplet collection or in-line detection procedure should eliminate this source of contamination.

TABLE 1

Quantitative PCR results for contamination at the inlet. 35.00 corresponds to no detectable cDNA, and each integer decrement corresponds to a doubling in the relative cDNA mass.

| No Silane | | Silane | | Silane + Surfactant | | Teflon + Surfactant | |
| --- | --- | --- | --- | --- | --- | --- | --- |
| Droplet | Q PCR Value | Droplet | Q PCR Value | Droplet | Q PCR Value | Droplet | Q PCR Value |
| cDNA | 19.90 | cDNA | 20.32 | cDNA | 20.29 | cDNA | 19.74 |
| Wash 1 | 32.99 | Wash 1 | 32.18 | Wash 1 | 32.89 | Wash 1 | 35.00 |
| Wash 2 | 35.00 | Wash 2 | 33.66 | Wash 2 | 34.36 | Wash 2 | 35.00 |
| Wash 3 | 32.15 | Wash 3 | 34.91 | Wash 3 | 34.77 | Wash 3 | 35.00 |
| Wash 4 | 32.54 | Wash 4 | 35.00 | Wash 4 | 35.00 | Wash 4 | 35.00 |
| Wash 5 | 35.00 | Wash 5 | 34.92 | Wash 5 | 35.00 | Wash 5 | 35.00 |
| Mix Reservoir | 33.15 | Mix Reservoir | 35.00 | Mix Reservoir | 35.00 | Mix Reservoir | 33.13 | | 35.00 |

TABLE 2

Quantitative PCR results for contamination during cycling in a silanized capillary with fluorosurfactant. 35.00 corresponds to no detectable cDNA, and each integer decrement corresponds to a doubling in the relative cDNA mass.

| Droplet | Q PCR Value |
| --- | --- |
| Control 1 | 35.00 |
| Control 2 | 35.00 |
| cDNA | 20.17 |
| Control 3 | 35.00 |
| Control 4 | 35.00 |
| Wash 1 | 35.00 |
| Wash 2 | 35.00 |
| Wash 3 | 35.00 |
| Wash 4 | 35.00 |
| Wash 5 | 35.00 |
| Mix Reservoir | 33.90 |

TABLE 3

Quantitative PCR results for contamination during cycling in a Teflon capillary with fluorosurfactant. 35.00 corresponds to no detectable cDNA, and each integer decrement corresponds to a doubling in the relative cDNA mass.

| Droplet | Q PCR Value |
| --- | --- |
| Control 1 | 35.00 |
| Control 2 | 30.19 |
| cDNA | 19.83 |
| Control 3 | 35.00 |
| Control 4 | 35.00 |
| Mix Reservoir | 35.00 |

EXAMPLE 16: DESIGN AND FABRICATION OF A CONTAMINATION FREE T-CONNECTOR

This example illustrates the conception of a PDMS T-connector 100 with a very low dead volume allowing to connect without contamination three different entries compatible with the use of pinch valves.

Figure 22:
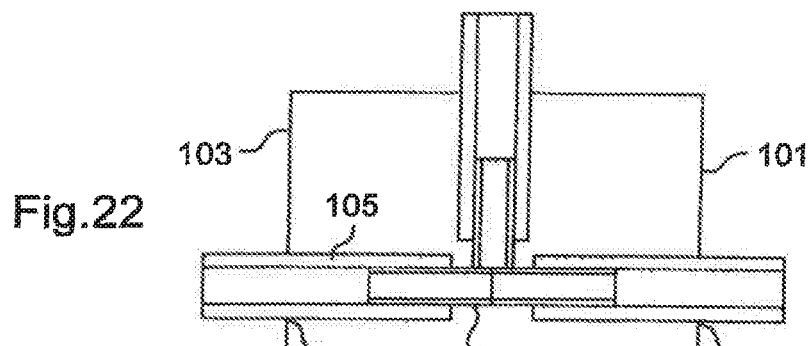
FIGS. 22 to 24 represent diagrammatically and partially a contamination free connector according to the invention.
Figure 23:
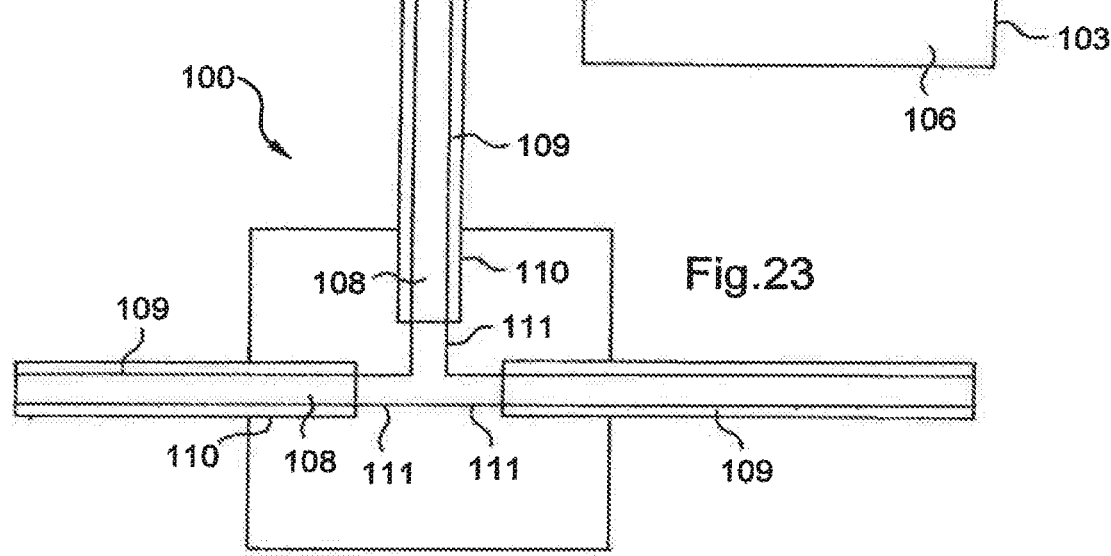
Figure 24:
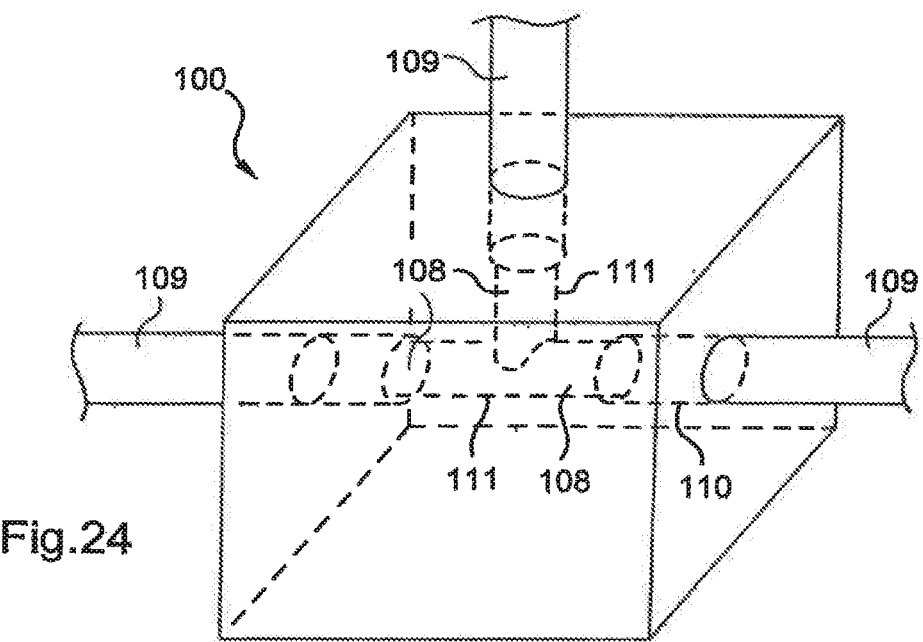

The connector 100 is made in PDMS (KODAK SYLGARD 184) with a 1:10 proportion of curing agent. The mould 101 used for manufacturing the connector 100 is a PMMA paralepiped (inner length and width 9 mm, inner height 8 mm). 800 µm inner diameter holes 102 are drilled on the center of three faces 103 of the paralepiped. A first 5 mm piece 104 of Teflon® capillary 105 (outer diameter 800 µm) is introduced inside the end of a 3 cm long second Teflon capillary (outer diameter 1.5 mm, inner diameter 800 µm) and sticks out on 1.5 mm. Three pieces are made this way and are introduced and maintained inside the paralepiped so as to form a T with the smaller tubing facing each other (see FIG. 22). The PDMS 106 is then degassed for 20 minutes, poured in the so constructed mould and put in a 65° C. oven for three hours.

After three hours, the Teflon® pieces 104 and 105 are taken off by gently pulling on them, and the obtained T-connector is taken out of the mould 101. The T-connector 100 has three ports 108, each comprising coaxial cylindrical hollow portions following each other, the outer one 110 having 1.5 mm diameter on a length of 3 mm, the inner one 111 having 800 µm diameter on a length of 1.5 mm. 5 cm silicone capillary tubes 109 (Cole-Parmer; outer diameter 1.8 mm, inner diameter 800 µm) coated with silicon rubber (Dow Corning) are then introduced on 3 mm (corresponding to the outer cylinder) in each hole of the T-connector, and the connector is strengthened by adding more rubber around the tube near the entry of the PDMS T. Due to silicon and PDMS elasticity, it is possible to push the 1.8 mm outer diameter silicon tubing in the 1.5 mm diameter hole of the T, thus providing a good tightness of the junction. The obtained connector is put in the oven for two hours.

The T-connector 100 with silicon capillary tube is further silanised with the method described in Example 14. A solid connector with very low dead volume and no leakage even under high pressure is obtained with this method. Furthermore, the use of silicon tube allows using pinch valves which have no dead volume.

EXAMPLES OF APPLICATIONS

A device made in accordance with the invention may be used to carry out, for instance:
  mixing,
  nucleic acid screening,
  nucleic acid amplification, e.g. by PCR, NASBA, rolling circle amplification
  RNA reverse transcription
  genotyping,
  proteomic analysis,
  transcriptome analysis,
  crystallization, and in particular protein crystallisation,
  searching and evaluation of pharmaceutical targets, pharmaceutical hits or leads, or drugs,
  enzyme-protein reaction,
  antigen-antibody reaction,
  screening of libraries of chemical of biological products,
  high throughput screening,
  drug delivery,
  diagnosis,
  analysis or lysis of at least one living cell or dead cell,
  analysis of microorganisms,
  chemical reaction,
  reactive-catalyzer reaction,
  polymerization reaction,
  fusing particles, for example colloids, to form a chain,
  preparation of colloids, emulsions, vesicles, in particular monodisperse colloidal objects,
  preparation of nanoparticules or microparticles,
  environmental control,
  detection of pollutants,
  control of an industrial process.

The invention claimed is:

1. A device for performing a PCR, comprising:
a microchannel comprising a coil comprising a capillary tube defining an internal space of the microchannel, wherein the capillary tube comprises a bulk fluorinated material that is non-internally coated, wherein the capillary tube is at least partly filled with:
a carrier fluid comprising a fluorosolvent containing a surfactant, and
aqueous droplets surrounded by the carrier fluid,
the coil comprising a denaturing region and an annealing region, both regions being at different temperatures, wherein the difference between an interfacial tension between a droplet and the capillary tube and an interfacial tension between the droplet and the carrier fluid is at least 26 mN/m.

2. The device according to claim 1, wherein the bulk fluorinated material is a fluoropolymer.

3. The device according to claim 1, comprising a cylinder comprising three regions corresponding to the denaturing, annealing and elongation regions.

4. The device according to claim 3, the capillary tube being wound around the cylinder.

5. The device according to claim 3, the denaturing, annealing and elongation regions being isolated one from another by sheets, which are affixed between the pieces of the cylinder.

6. The device according to claim 3, the size of the elongation region being twice the size of the denaturing and annealing regions.

7. The device according to claim 1, the device having a cylinder shape and comprising three ventilation holes per quarter cylinder, said holes being drilled through the entire device to provide vents for air cooling.

8. The device according to claim 7, further comprising a turbine configured to blow ambient air through the ventilation holes providing temperature control and uniformity.

9. The device according to claim 1, the device having a cylinder shape, two holes for receiving thermocouples and one central hole for receiving a heater being drilled partially through the cylinder in each temperature region, the central hole being larger than the holes for receiving the thermocouples.

10. The device according to claim 1, each region comprising a resistance heater and two thermocouples.

11. The device according to claim 10, the resistance heaters being located in the center of their respective region, and the thermocouples being located near the interface between regions.

12. The device according to claim 1, the capillary tube comprising a DNA fragment.

13. The device according to claim 1, wherein the coil comprises an elongation region being at a temperature different from the temperature of the denaturing and the annealing regions.

* * * * *